(12) United States Patent
Robbins et al.

(10) Patent No.: US 8,615,790 B2
(45) Date of Patent: *Dec. 24, 2013

(54) MANAGING SECURE SHARING OF PRIVATE INFORMATION ACROSS SECURITY DOMAINS USING MULTIPLE CASELOADS

(75) Inventors: Richard Allen Robbins, New York, NY (US); Warren Stanton Gifford, Long Branch, NJ (US); Mojahedul Hoque Abul Hassnat, Block E. Banani (BD); Bradley Drew Turock, Hillsborough, NJ (US); Justin Mark Brockie, Wolcott, CT (US); James Michael Kelly, Woodbury, CT (US); Ziaur Rahman, Gulshan-2 (BD)

(73) Assignee: Therap Services LLC, Waterbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,388

(22) Filed: Aug. 31, 2012

(65) Prior Publication Data

US 2013/0007897 A1 Jan. 3, 2013

Related U.S. Application Data

(62) Division of application No. 11/604,577, filed on Nov. 27, 2006, now Pat. No. 8,281,370.

(51) Int. Cl.
*G06F 17/30* (2006.01)
*G06F 15/16* (2006.01)

(52) U.S. Cl.
USPC .............................................. 726/4; 709/218

(58) Field of Classification Search
None
See application file for complete search history.

(56) References Cited

U.S. PATENT DOCUMENTS

| | | | |
|---|---|---|---|
| 5,867,821 A * | 2/1999 | Ballantyne et al. | 705/2 |
| 6,988,075 B1 * | 1/2006 | Hacker | 705/3 |
| 7,334,254 B1 * | 2/2008 | Boydstun et al. | 726/2 |
| 7,490,048 B2 * | 2/2009 | Joao | 705/3 |
| 8,042,160 B1 * | 10/2011 | Boydstun et al. | 726/6 |
| 8,275,632 B2 * | 9/2012 | Awaraji et al. | 705/2 |
| 2001/0041991 A1 * | 11/2001 | Segal et al. | 705/3 |
| 2002/0004727 A1 * | 1/2002 | Knaus et al. | 705/3 |
| 2002/0169876 A1 * | 11/2002 | Curie et al. | 709/226 |
| 2004/0199765 A1 * | 10/2004 | Kohane et al. | 713/165 |
| 2006/0036468 A1 * | 2/2006 | Thomas et al. | 705/1 |
| 2007/0211762 A1 * | 9/2007 | Song et al. | 370/490 |
| 2007/0271598 A1 * | 11/2007 | Chen et al. | 726/4 |

* cited by examiner

*Primary Examiner* — Cordelia Zecher
*Assistant Examiner* — Abdullah Almamun
(74) *Attorney, Agent, or Firm* — James R. Klaiber; Pryor Cashman LLP

(57) ABSTRACT

In a method of granting a user in a first organization access to private information stored within an authorization profile of a second organization, an access agreement between the two organizations is formed. Authorization is requested for the user, the authorization profile is retrieved, and authorization to private information is granted if authorized by the access agreement.

In a method of authorizing access by users to private information stored by an organization as associated with a program, three types of caseloads are defined. The first authorizes access to information of a first individual of a first program, the second authorizes access to information of a second individual of all programs, and the third authorizes access to information of all individuals of a second program. Authorization is requested for the user to access one or more of the caseloads, and access to one or more caseloads is granted to the user.

10 Claims, 29 Drawing Sheets

Activity Tracking 3341 items found, displaying 1 to 20.
First | Previous | 1|2|3|4|5|6|7|8|9|10 | Next | Last

| Login Name | IP Address | Action | Module Name | Action | Form ID | Date | Program | Comments |
|---|---|---|---|---|---|---|---|---|
| User A | 59.152.1.240 | Logon | | | | Jan 31, 2006 4:13:00 AM | | Logon: Mozilla/4.0 (compatible; MSIE 6.0; Windows NT 5.1; SV1; FunWebProducts) |
| User B | 59.152.1.240 | Logon | | | | Jan 31, 2006 3:31:23 AM | | Logon: Mozilla/5.0 (Windows; U; Windows NT 5.1; en-US; rv:1.7.6) Gecko/20050223 Firefox/1.0.1 |
| User C | | | Secure Communications | Message Send | | Jan 31, 2006 3:30:08 AM | | |
| User A | | | Secure Communications | Message Send | | Jan 31, 2006 3:30:07 AM | | |
| User C | 59.152.1.240 | Notif Info Changed | | | | Jan 31, 2006 2:10:22 AM | | Mozilla/5.0 (Windows; U; Windows NT 5.1; en-US; rv:1.8) Gecko/20051111 Firefox/1.5 |
| User A | 59.152.1.240 | Logon | | | | Jan 31, 2006 2:09:33 AM | | Logon: Mozilla/5.0 (Windows; U; Windows NT 5.1; en-US; rv:1.8) Gecko/20051111 Firefox/1.5 |
| User B | | | Secure Communications | Message Send | | Jan 31, 2006 2:09:17 AM | | |
| User D | 59.152.1.240 | User Privilege Updated | | | | Jan 31, 2006 2:09:17 AM | | Mozilla/5.0 (Windows; U; Windows NT 5.1; en-US; rv:1.8) Gecko/20051111 Firefox/1.5;User:rajiv |
| User C | 59.152.1.240 | Super Role Created | | | | Jan 31, 2006 2:07:51 AM | | Mozilla/5.0 (Windows; U; Windows NT 5.1; en-US; rv:1.8) Gecko/20051111 Firefox/1.5;Super Role:special |
| User D | 59.152.1.240 | Logon | | | | Jan 31, 2006 2:07:18 AM | | Logon: Mozilla/5.0 (Windows; U; Windows NT 5.1; en-US; rv:1.8) Gecko/20051111 Firefox/1.5 |
| User A | 59.152.1.240 | Logon | | | | Jan 31, 2006 2:03:35 AM | | Logon: Mozilla/5.0 (Windows; U; Windows NT 5.1; en-US; rv:1.7.6) Gecko/20050223 Firefox/1.0.1 |
| User A | 59.152.1.240 | Logon | | | | Jan 31, 2006 1:57:36 AM | | Logon: Mozilla/4.0 (compatible; MSIE 6.0; Windows NT 5.1; SV1; FunWebProducts) |
| User D | 59.152.1.240 | Logon | | | | Jan 31, 2006 12:33:53 AM | | Logon: Mozilla/5.0 (Windows; U; Windows NT 5.1; en-US; rv:1.7.6) Gecko/20050223 Firefox/1.0.1 |
| User C | 59.152.1.240 | Logon | | | | Jan 31, 2006 12:33:45 AM | | Logon: Mozilla/4.0 (compatible; MSIE 6.0; Windows NT 5.1; SV1) |
| User C | 59.152.1.240 | Logon | | | | Jan 31, 2006 12:12:18 AM | | Logon: Mozilla/4.0 (compatible; MSIE 6.0; Windows NT 5.1; SV1; .NET CLR 1.1.4322) |
| User A | 59.152.1.240 | Logon | | | | Jan 30, 2006 11:59:04 PM | | Logon: Mozilla/4.0 (compatible; MSIE 6.0; Windows NT 5.1; SV1; FunWebProducts) |
| User E | 59.152.1.240 | Logon | | | | Jan 30, 2006 11:47:07 PM | | Logon: Mozilla/4.0 (compatible; MSIE 6.0; Windows NT 5.1; SV1; .NET CLR 1.1.4322) |
| User B | 59.152.1.240 | Logon | | | | Jan 30, 2006 11:45:20 PM | | Logon: Mozilla/4.0 (compatible; MSIE 6.0; Windows NT 5.1; SV1; .NET CLR 1.1.4322) |
| User A | 59.152.1.240 | Login Failure | | | | Jan 30, 2006 11:44:47 PM | | Password Mismatch |
| User D | 59.152.1.240 | Logon | | | | Jan 30, 2006 11:44:22 PM | | Logon: Mozilla/5.0 (Windows; U; Windows NT 5.1; en-US; rv:1.7.6) Gecko/20050223 Firefox/1.0.1 |

New Search

Therap — Notification Configuration

Module Name: General Event Reports
CaseLoad Name: Caseload-All-Programs

Notification Events

| Event | Send Notification |
|---|---|
| Submit | ○ Yes ● No |
| Approve | ○ Yes ● No |
| Delete | ○ Yes ● No |
| Return | ○ Yes ● No |
| Review | ○ Yes ● No |
| Follow-up | ○ Yes ● No |

Jump to section: 2

Select Media

Numeric Pager

| | | | | |
|---|---|---|---|---|
| Injury | ○ High | ○ Medium | ○ Low | ● No |
| Medication Error | ○ High | ○ Medium | ○ Low | ● No |
| Restraint Related to Behavior | ○ High | ○ Medium | ○ Low | ● No |
| Restraint Other | ○ High | ○ Medium | ○ Low | ● No |
| Death | ○ High | ○ Medium | ○ Low | ● No |
| Other | ○ High | ○ Medium | ○ Low | ● No |
| Abuse | ○ Yes | ● No | | |
| Neglect | ○ Yes | ● No | | |
| Internal Report (Yes) | ○ High | ○ Medium | ○ Low | ● No |
| Internal Report (No) | ○ High | ○ Medium | ○ Low | ● No |

Text Pager/Cell Phone

| | | | | |
|---|---|---|---|---|
| Injury | ○ High | ○ Medium | ○ Low | ● No |
| Medication Error | ○ High | ○ Medium | ○ Low | ● No |

Jump to section: 1

Configure Password Policy

Configure Password Policy

Minimum length of password: 6
Minimum number of upper-case letters: 1
Minimum number of digits: 1
Minimum number of other characters (!@#$%^&*:;', etc.): 0
Maximum number of incorrect passwords tolerated (Set to '0' to disable Account Locking): 0
Time-frame for incorrect passwords: 0 Minute(s)
Expiry age of a password in days (Set to '0' to disable Password Aging): 182
Starting day of warning to user before expiration: 3

Cancel    Save  Restore Defaults

Figure 16a

MANAGING SECURE SHARING OF PRIVATE INFORMATION ACROSS SECURITY DOMAINS USING MULTIPLE CASELOADS

This divisional application claims priority on prior filed U.S. non-provisional application Ser. No. 11/604,577 filed Nov. 27, 2006. All description, drawings and teachings set forth therein are expressly incorporated by reference herein and claim to priority upon the teachings expressly made herein.

FIELD

Embodiments of the invention relate to managing secure sharing of private information across security domains. This is widely applicable, and is especially critical to healthcare applications to comply with Health Insurance Portability and Accountability Act of 1996 ("HIPAA")—a set of standards and requirements for the electronic transmission of certain health information implemented to increase the efficiency and effectiveness of the health care system; this is particularly challenging for Individuals with developmental disabilities (DD). Embodiments of the invention are also applicable with respect to other regulations—for example, financial services regulations—as well as other laws, standards, and policies—for example, proprietary information for different portions of a project. The uniqueness in embodiments of this invention is in its ability to share information among authorized users across different organizations and security domains, without requiring direct contact among security administrators in different domains, and yet still complying with security requirements.

BACKGROUND

In applications requiring privacy or security of electronic information, the state of the art is using rule-based security access, with a variety of recognition systems for each user. Unfortunately, this does not include a system for maintaining the security of information when it is electronically shared among different security domains.

Typically, information may be shared securely among organizations in paper format because of a lack of compatible electronic formats and appropriate privacy and security systems. The desired information may be physically copied and delivered. This makes it prone to delays, missing information, unregistered users, lack of clarity of what information is authorized to be transmitted, and unauthorized access by different people. All these are challenges with the current physical system in complying with security protocols.

As stated in the HIPAA regulations, rule-based security systems with passwords is the target practice. These systems are widely used throughout the government and industry. However they do not address how to actively share information across security domains managed separately. In many hospitals, the combination of being unable to predict who may need to provide care, especially in an emergency, and the challenges of maintaining a variety of accounts and passwords, each with limited access, results in each doctor and health professional being provided with access to all patients' information throughout the institution. These practices may expose healthcare providers to potential liability for not properly protecting sensitive Individual health information.

This is particularly challenging for Individuals with Developmental Disabilities, which are lifelong conditions with varying degrees of impairments. Individuals are often subject to more medical and other health conditions, and may have more emergencies. They may have others designated to act on their behalf in various capacities including medical, financial, and legal. Access to Personal Health Information ("PHI") about health and related conditions is strictly regulated by HIPAA and other state and federal regulations, which complicates providing support and services.

Care and support for Individuals with Developmental Disabilities is often distributed among many people and organizations, including Parents, service providers, doctors and other health professionals, volunteers, and case managers and others appointed by various funding and regulatory jurisdictions. The responsibilities and privileges of different users (ranging from Parents or Guardians to health care professionals and staff members) may differ by funding sources and organizational structures, and thus a flexible system for determining who has access to what information is essential. For example, often an organization providing support to an Individual may have different groups with separate staff to provide different functions, and thus processes may be used to control who has access to what information by application and Individual; also a staff member with specialized capabilities, such as a behaviorist, has responsibilities that cut across other organizational boundaries and serve one or a few Individuals out of each grouping. Individuals often change the organizations which provide support for them and thus users wish to be provided access to appropriate information covering past conditions and situations from other organizations. HIPAA and other regulations request that Individuals and their agents be able to update their PHI records. Changes in information may need to be shared and maintained among a range of people and authorities over many decades.

In the face of such challenges it becomes difficult for care providers to manage privacy and security of information and communications about the Individuals they serve, particularly in accordance with HIPAA regulations. Such limitations urgently call for a system that can facilitate secure entry, access, sharing, updating, storage, and management of information about an Individual.

Similar situations exist in many other industries. Banking and credit where many different organizations use and create information about people with a critical need for security and privacy. Proprietary information within and among organizations regarding product development, marketing, sales, and other areas of operations also benefit from such a system.

SUMMARY

Embodiments of the invention provide systems for managing inter-domain (among multiple security domains) and intra-domain (within the security domain) sharing of secure information intended to meet security and privacy regulations. Embodiments of this invention may have applications for sharing and managing, inter alia, PHI across and within organizations in the Developmental Disability community, in compliance with HIPAA and other regulations and security procedures.

Embodiments of this system ensure that Individual information is securely stored, eliminating the risk of loss of information. It allows users to record Individual information to a database making the information securely available any time, anywhere to users who have authorization to access the information, including special provisions for emergencies. Users in different security domains may access information and perform actions depending on the roles and privileges assigned by the administrators in all the relevant security domains.

Embodiments of the system disclosed in this document provide ways of sharing private health information and ensuring a means to restrict any unauthorized access or sharing of such information across different security domains, so that each security manager is responsible for users in their own domain, and yet may specify the level of access for users in other domains.

Accomplishing this involves algorithms to assure that any sharing is appropriately authorized, that Individuals are correctly matched among security domains, that emergency access is provided appropriately, that archived information is appropriately managed, and that all accesses and changes are tracked in accordance with security requirements.

According to one embodiment of this invention, the Individual or their Guardian may be given control of the information by being the Primary Security Domain and controlling the Archived information. The Individual or their Guardian may then manage who has access to information, who may store it, and may even update it.

BRIEF DESCRIPTION OF THE FIGURES

FIG. 3a is a sample screenshot of a Regulator or Funder Service Authorization Form

FIG. 5a is a sample of an Individual Data Form screenshot.

FIG. 6a is a sample screenshot of a page where Caseloads are defined.

FIG. 7a is a sample screenshot of a page where Security Access Roles are defined.

FIG. 8 is a sample screenshot of a page where Security Access Privileges are assigned to authorized users.

FIG. 11a is a sample screenshot of the records saved securely to facilitate Tracking Changes in Information caused by user activities.

FIG. 12a is a screenshot of the 'FirstPage' from where authorized users get notified of their required task.

FIG. 12b is a screenshot of Notification Information that are required by the system in order to provide appropriate notifications to authorized users.

FIG. 12c is a sample of the Notification Profile screenshot which enables alerting authorized users of activities in their authorized services.

FIG. 13a is a sample of Secure Access to Shared Archived Individual information pages that enable authorized users to share and access archived data in a secure environment.

FIG. 14a is a sample of an Emergency Data Form Role screenshot that displays the individual information requested in emergency situations.

FIG. 15 is a sample of Additional Shared Security Feature screenshot that ensure absolute privacy in sharing.

FIG. 16a is a sample of the 'Security Monitoring and Auditing for Shared Access' pages that enable systems to monitor and audit the security for shared access.

DETAILED DESCRIPTION OF THE INVENTION

The disclosed system on information sharing enables users among different organizations in different security domains to access, inter alia, PHI based on rules governed by HIPAA, as well as other laws, regulations, standards, and/or policies. Information sharing for common Individuals may be between users in two or more organizations or within different security domains in one organization.

Figure 1:
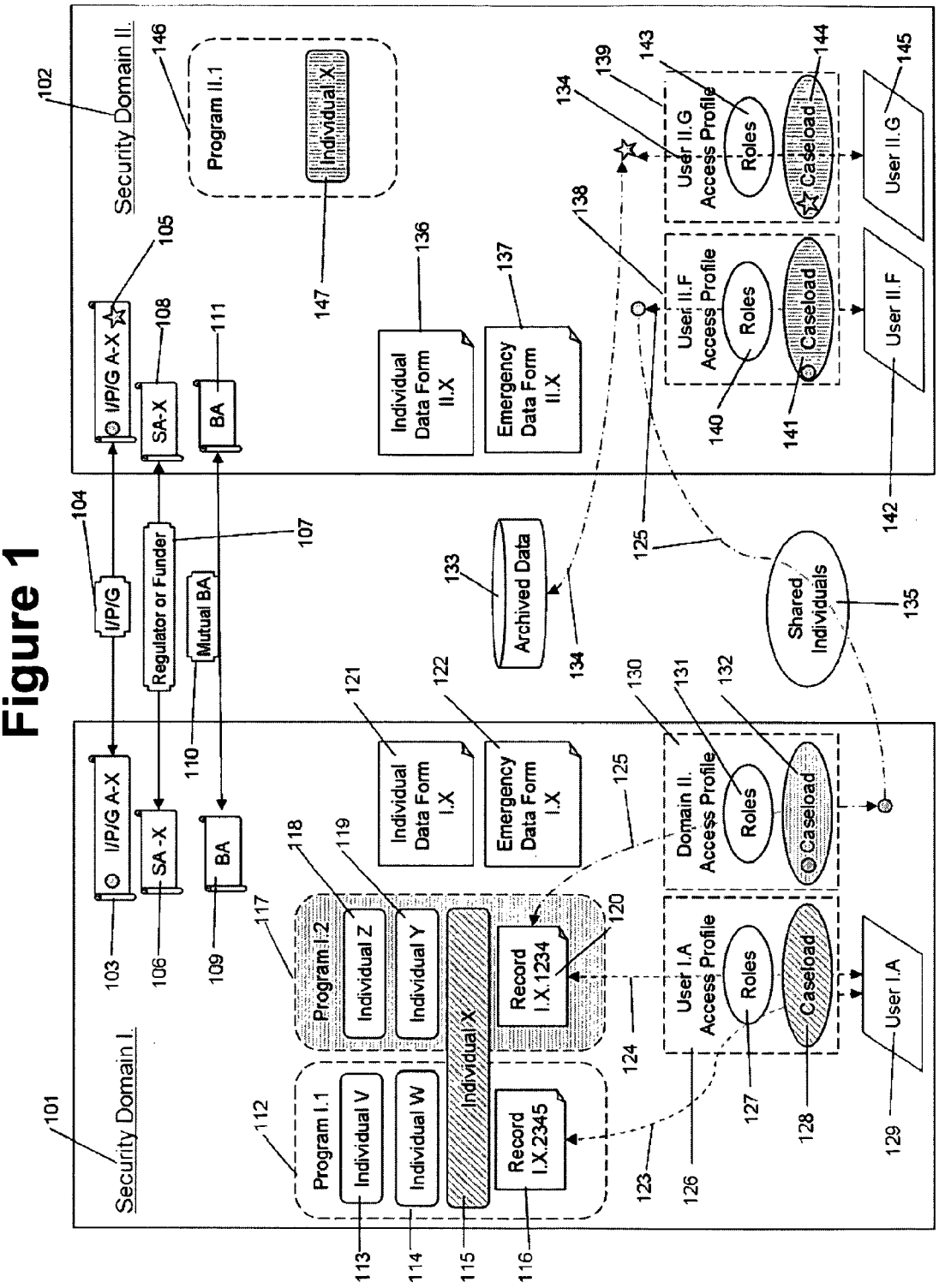
FIG. 1 illustrates an overview of embodiments of the disclosed system of managing Secure Sharing of Private Information Across Security Domains.

FIG. 1 illustrates an overview the embodiments of the invention (Secure Shared Information Access)

As shown in FIG. 1, Security Domains I 101 and II 102 represent two different organizations. In the figure, Individual X (115 and 147) represents an Individual who is served by both organizations, Security Domain I 101 and Security Domain II 102. Individual X 115 may be different from Individual X 147 as they represent Individual X in the respective Domains (not X themselves)

Each Security Domain may have a valid Individual, Parent, or Guardian Authorization (I/P/G A-X) (103 in Security Domain I; 105 in Security Domain II) to store or access private information about Individual X, and also to share information with another organization. The Individual/Parent/Guardian (I/P/G) 104 may provide authorization to the organizations to access information about Individual X. The organizations may, optionally, receive Service Authorizations (SA-X) 106 (in Security Domain I) and 108 (in Security Domain II) from Regulators or Funders 107 that define the services which may be provided for Individual X. These two organizations 101 and 102 may also enter into a Business Agreement (BA) 109 (in Security Domain I) and 111 (in Security Domain II) that may comply with privacy, and security regulations in accordance with HIPAA, or other laws, regulations, standards, or policies. Embodiments of this invention include systems for assuring that these Authorizations and mutual Business Agreements 110 are appropriately executed (if the organization executes such an agreement). Once the terms and conditions have been agreed on, a mutual Business Agreement 110 may be formed and the organizations may proceed to, share information on an Individual that is supported by both, and authorized for sharing.

Central to all modes of information sharing defined by the system, is the prior state of the art system of assigning access privileges to users. Access privileges control users' access to specific Individual information. The information that may be shared and the actions that may be performed on Individual information may depend on the access privileges or roles assigned to the authorized users. Users may be able to access and share selected Individual information based on the roles.

Referring to FIG. 1, both the organizations have detailed information on Individual X (115 and 147) in Individual Data Form I.X 121 and Emergency Data Form I.X 122 in Security Domain I 101, and Individual Data Form II.X 136 and Emergency Data Form II.X 137 in Security Domain II 102. In Security Domain I 101, Individual X 115 is enrolled in two service Programs, termed as Program I.1 112 and I.2 117. These programs (Program I.1 112 and I.2 177) also represent different security domains which are within the same organization. The same Individual, represented as Individual X 147 is also enrolled in Program II.1 146 in Security Domain II 102. Security Domain I 101 has a Sharing Access Profile 130 which governs access from users in Security Domain II 102 Embodiments of this invention include systems to identify common individuals and their corresponding health information that may be shared.

Access profiles, for example User I.A Access Profile 126, control what a user may do. The access profile is defined by a combination Caseload, for example Caseload 128, which defines what information for which individuals may be accessed, and by Roles, for example Role 127, which specify the functions which may be accessed by the user for each application. The system also defines Domain II Access Profile 130 for sharing across Security Domains of various organizational boundaries.

Embodiments of this invention also include systems allowing users in one organization to access individual information under different security domains within that same organization. Such a system for augmenting prior art security management arrangements is referred to as "Caseloads," which allow the security manager to define access protocols and thus specify the access capabilities of the user. Caseloads may be categorized as two types: Standard Caseloads and Super Caseloads. Standard Caseloads may be mapped to:
(1) All the individuals in one Program, as shown, for example, in Caseload 132 and indicated by horizontal shading for Program I.2 117;
(2) One Individual in all Programs in the Security Domain I, as shown in Caseload 128 and indicated by diagonal shading for Individual X 115 in Programs I.1 112 and I.2 117.
(3) One individual in one Program, as shown in Caseload 141 and indicated by vertical shading for Individual X 147 in Program II.1 146;

Super Caseloads are defined as a set of Standard Caseloads. In the case of a Super Caseload, a Standard Caseload may be added to a newly created Super Caseload. This means all the groups of Programs, Program-Individual pairs, and Individuals under the former Standard Caseload may now become a subset of the new Super Caseload. Moreover, if changes are made to the former Standard Caseload, those changes may be reflected in the new Super Caseload as well. For example, if a new Individual is added to a Program, or an existing Individual is added to a new Program, then this automatically is incorporated in cases (1) and (3), respectively, for both the Standard Caseloads and for the Super Caseloads including these Standard Caseloads.

The system also provides embodiments for Internal Domain Access Sharing of Individual information within an organization. Referring to FIG. 1, User I.A 129 is an authorized user in Security Domain I 101, and User II.F 142 and User II.G 145 are authorized users in Security Domain II 102. Each may have similar or different access profiles under the security domains they are in. User I.A 129 in Security Domain I 101 has access privileges on Individual X 115. This means that embodiments of the invention allow User I.A 129 to access records 116 and 120 of Individual X 115 irrespective of the programs Individual X 115 is enrolled in within Security Domain I 101. That is, User I.A 129 may access Record I.X.2345 116 in Program I.1 112 and Record I.X.1234 120 in Program I.2 117 of Individual X 115. Accessibility is represented by arrows 123 and 124.

The conventional program-based security access system has a user who is assigned privileges for different programs within an organization. Individuals Z 118, Y 119 and X 115 are enrolled in Program I.2 117 within the organization Security Domain I 101. Individual X 115 is also enrolled in Program I.1 112 along with Individual V 113 and Individual W 114. User I.A 129 has been given roles 127 and access privileges for Program I.2 117.

For example, a different user having a different Access Profile may be given roles and access privileges only for Program I.2 117. This means that embodiments of the invention allow this user to access information for all Individuals enrolled in the Program I.2 117. In the case of User I.A 129, apart from accessing information on Individual X 115 (Record I.X.2345 116 in FIG. 9) in Program I.1 112, User I.A 129 can also access the information of Individual X 115 (Record I.X.1234 120 in FIG. 9) entered by the different user in Program I.2 117. The actions User I.A 129 may perform on Individual X's information in Program I.2 117 may depend on the union of all the Roles 127 in the Caseload 128 that have been assigned.

For example, User I.A 129 in Security Domain I 101 is assigned by the Data Administrator the Submit and Approve roles for a particular application. As shown in FIG. 1, User I.A 129 has been assigned the caseload 128 on Individual X 115 enrolled in Programs I.1 112 and I.2 117. Embodiments of this invention may ensure security by automatically checking the controllability of the authorized user and thus providing the user the access accordingly. The Submit Role may include privileges that allow authorized users to enter, save and submit the information. Information that has been saved may be edited and saved again by User 1.A 129. Once the information has been submitted, it moves to Submitted state and the originator having the Submit role may no longer have access to it. There may be certain applications that either request or do not request approval from users of certain privileges to ensure that the information entered on an Individual is accurate and meet the guidelines necessary to serve the Individual in the organization. If the application for which User I.A entered information requests approval, then the information in Submitted state awaits for approval. The Approve role allows the authorized User I.A to review the information and make necessary changes. The information may again be submitted for approval, or may be directly approved by the approver. However, if the application for which User I.A 129 entered information does not request approval, submitting the information for that application may result in saving it directly in a secure database of the system. This means that with the Submit and Approve roles in the Caseload on Individual X 115, embodiments of this invention may allow User I.A 129 to submit and approve information on Individual X in Programs I.1 112 and I.2 117.

With the Mutual Business Agreements 110 and Service Authorizations (SA-X 106 and 108) in effect, embodiments of the invention allow both the organizations to share information on common Individual—Individual X (115 and 147) among them. User II.F 142 in Security Domain II 102 has privileges to access information of Individual X 146 within Security Domain II 102, because the corresponding caseload 141 includes Individual X 115. Furthermore, User II.F 142 is authorized for access to Inter domain sharing, as indicated by the "shaded circle" in the Access Profile 141 and elsewhere. The Access Profile of Domain II 130 in Security Domain I 101 defines privileges for users in Security Domain II 102 to access information of common Individuals in Program I.2 117 of Security Domain I 101. That is, the Access Profile of Domain II 130 in Security Domain I 101 define Roles 131 for User II.F 142, in Security Domain II 102 for shared information on Individual X 115. Embodiments of the invention use systems to determine the common Individuals 135 among the organizations. Through this system the Access Profile of Domain II 130 in Security Domain I 101 may allow User II.F 142 in Security Domain II 102 to have access privileges on information of Individual X 115 in Program I.2 117 in Security Domain I 101. The actions that may be performed on such information depend on the intersection of the roles assigned to the user, defined in the Access Profiles in security Domains I 130 ∧ II 138. Thus, User II.F 142 in Security Domain II 102 may—through secure information sharing 125—have access to Record I.X.1234 120 in Program I.2 117 in Security Domain I 101 of Individual X 115. Embodiments of the invention control the access and sharing of information on Individual X 115 according to the regulations as agreed upon by both organizations. Thus, with respect to health information, embodiments of the invention are conforming to the privacy and security of Individual information as requested by the guidelines of HIPAA regulations.

Access profile of User II.G 139 in Security Domain II 102 may allow the user to have access privileges 134 on the Archived Data 133 of Individual X 115, as indicated by the "shaded star" in Access Profile 144 and elsewhere.

Figure 2:
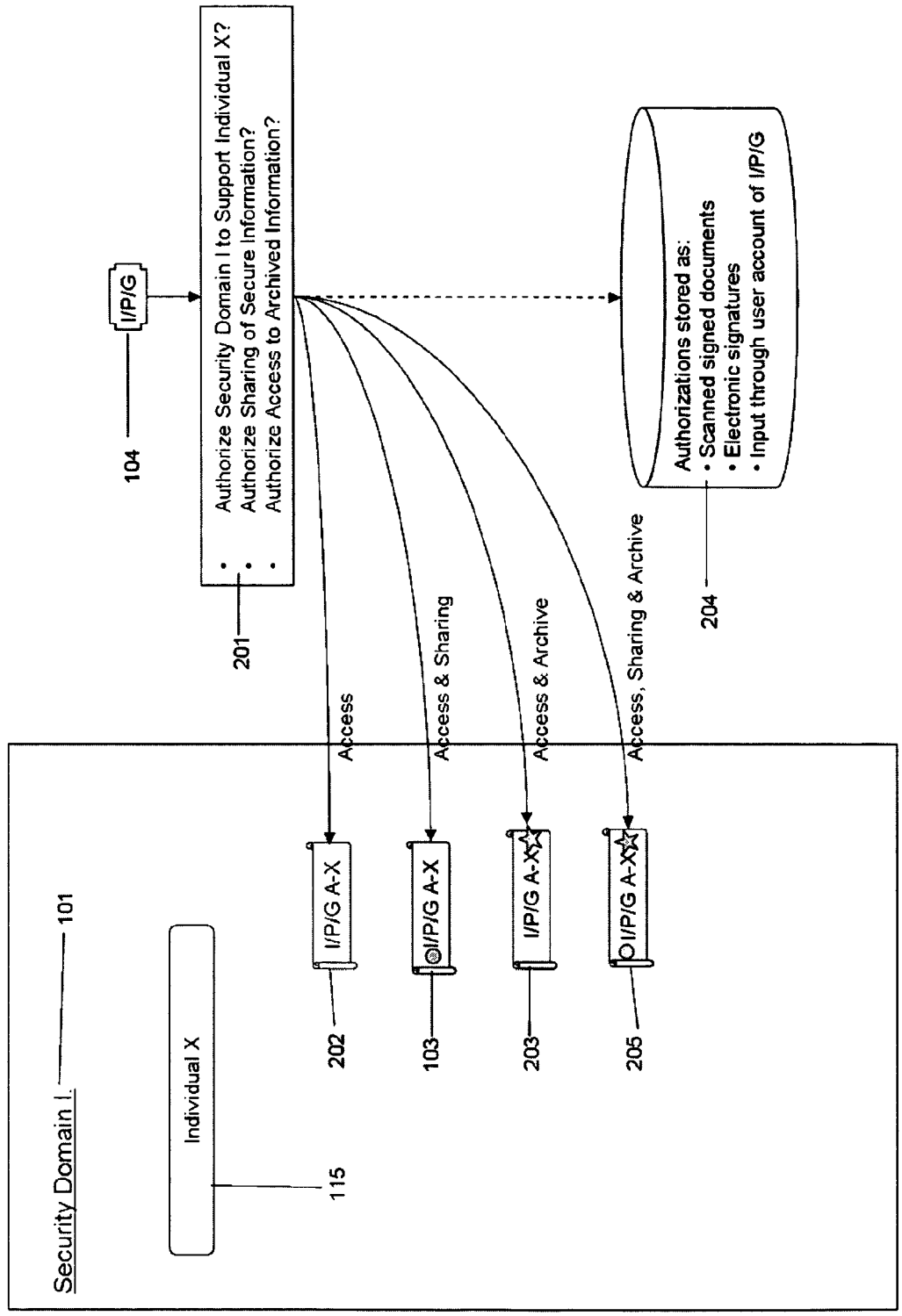
FIG. 2 illustrates embodiments of the Individual/Parent/Guardian Private Information Authorization Process.

FIG. 2 illustrates embodiments of the Individual, Parent and/or Guardian Private Information Authorization process. In order to share private information on an Individual between organizations it is essential to acquire the Individual's, Parent's or Guardian's (I/P/G 104) authorization.

With respect to Personal Healthcare Information (PHI), the conventional procedure is to obtain authorization by having the Individual, Parent and/or Guardian sign paper documents complying with HIPAA regulations. Typically these documents do not specify which organizations are authorized to receive information from the organization with the document, they are not readily updated, and they do not address storage and updating of private information.

Referring to FIG. 2, Individual X 115 represents the Individual to be enrolled in an organization. I/P/G 104 may authorize (201) a specific organization, Security Domain I 101, to provide service to Individual X 115, and to gather and access private information. That is, Security Domain I 101 may acquire I/P/G A-X 202 to access private information requested to serve Individual X 115. Further authorizations (I/P/G A-X 103) may also be allowed by I/P/G 104 for sharing of Secure Information with other authorized organizations, or authorization (I/P/G A-X 203) providing access to Archived Information, or authorization for all of the services mentioned above (I/P/G A-X 205).

Embodiments of the invention may provide systems for authorizations to be explicitly stored through user accounts, electronic signatures or scanned paper documents (204) so that I/P/G 104 may control private information access and sharing. Embodiments of the invention further enhance the authorization procedure by providing user accounts for I/P/G 104. Such authorizations include the authorization requested for an organization to provide service to the Individual and collect Private information, the authorization to access and share private information, and the authorization to access and archive information. By allowing I/P/G 104, or any combination thereof ongoing secure access to these authorizations, they may be reviewed and changed at any time.

Embodiments of the invention also deal with the situation where the Individual, Parent, and/or Guardian terminates the Authorization, either by deliberate intervention or by going beyond the specified duration of the Authorization without renewing it. As soon as the Authorization is terminated, all activities regulated by the Authorization are no longer allowed by the system. Note that this does not mean the information is destroyed, merely that the access and other authorizations related to it are terminated.

Figure 3:
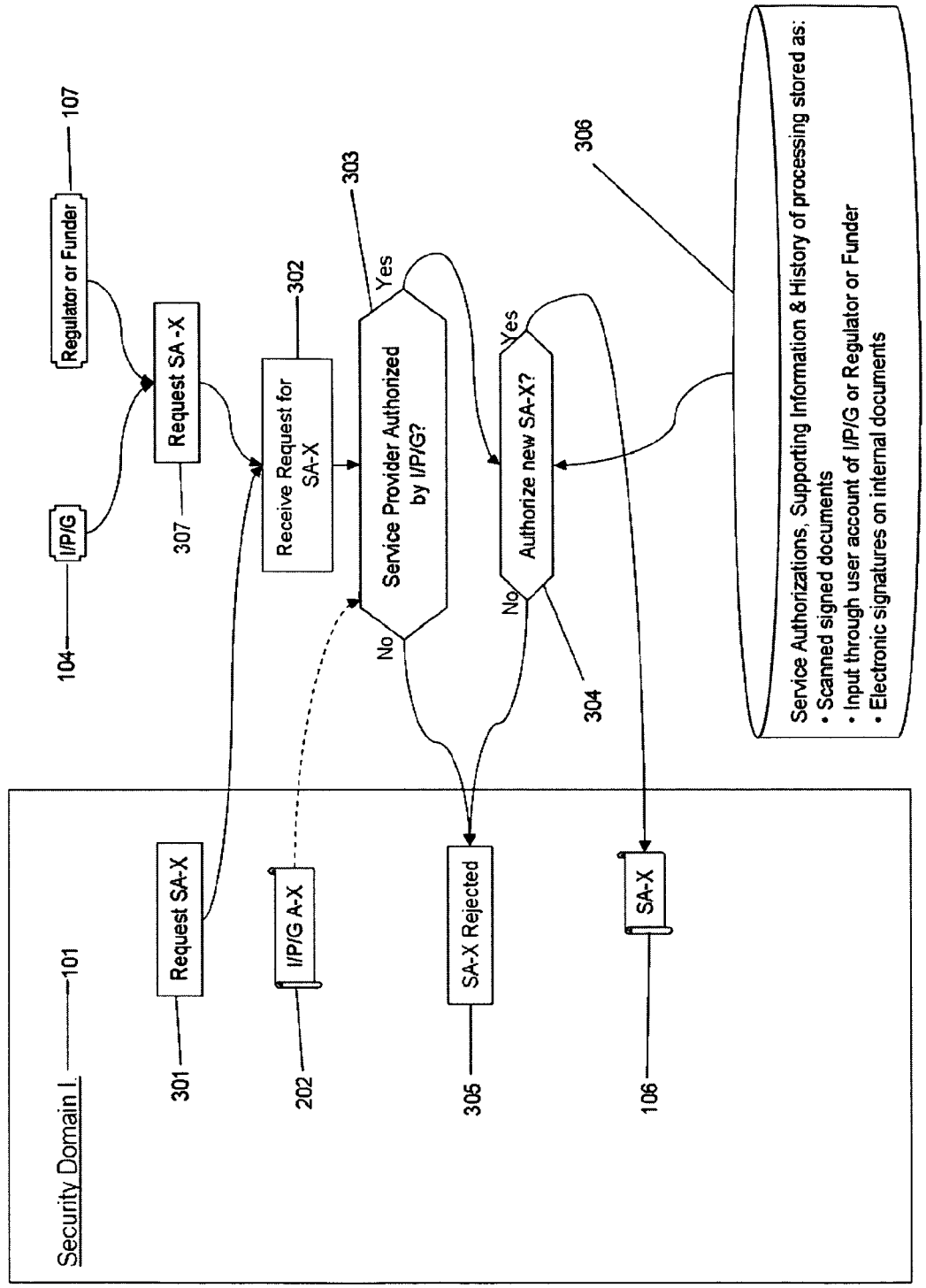
FIG. 3 illustrates embodiments of the Regulator or Funder Service Authorization Process.

FIG. 3 illustrates the Regulator or Funder Service Authorization Process. As part of the process of administering services, organizations providing services may obtain authorization to provide specific services from the regulating or funding organizations. To accomplish this, the different organizations may engage in a process to reach agreement on services to be offered while sharing private information securely.

Embodiments of the invention provide a secure system for the approval of service authorizations to be an integral part of the process of accessing, using, and sharing private information. Embodiments of the invention allow for agents of the regulating or funding organization to have these service authorization requests integrated with their own workflow even across many service organizations: notifying them of pending requests for authorizations; providing a system for secure communications to discuss and resolve differences, both within their organization, and with the funding organization, the Individual, Parents, and/or Guardians; providing a secure system for approving and/or rejecting; recording the outcome of all discussions and/or decisions; and sharing the approvals securely with the appropriate organizations. The service provider may also have the authorization request and approval process integrated with their work flow as well. In addition, when the Service Authorization has been approved, it may be automatically integrated with the work flow of providing and billing for services.

As shown in FIG. 3, an organization, such as Security Domain I 101, may request for Service Authorization of Individual X 301. Alternatively, the request for service authorization (SA-X 307) may come from the Individual, Parent, or Guardian or from within the regulating or funding organization. The agents may receive these requests (302). While processing the request SA-X 301 or SA-X 307, embodiments of the invention check to see if the Service Provider has been authorized (303) by the Individual, Parent, and/or Guardian to support Individual X. If the Service Provider is not authorized, the Service Authorization request may be rejected (305). If the Service Provider is authorized by the Individual, Parent, and/or Guardian, the Regulator or Funder may consider the Service Authorization (SA-X) 304 based on the information provided by the Service Provider and other information (306). Once the Service Authorization SA-X 106 is approved, it may be stored in a secure database 306. To accommodate Funding and Regulatory agencies that are not using the system, approvals may be entered in a variety of manners, including scanned signed documents and electronic signatures (306). When Regulators and Funders (107) access the system through user accounts, embodiments of the invention enhances the process.

Embodiments of the invention may also deal with the situation where the Funder or Regulator terminates the Service Authorization, either explicitly or by going beyond the specified duration of the Service Authorization without renewing it. As soon as the Service Authorization is terminated, all activities regulated by the Service Authorization are no longer allowed by the system.

Figure 3A:
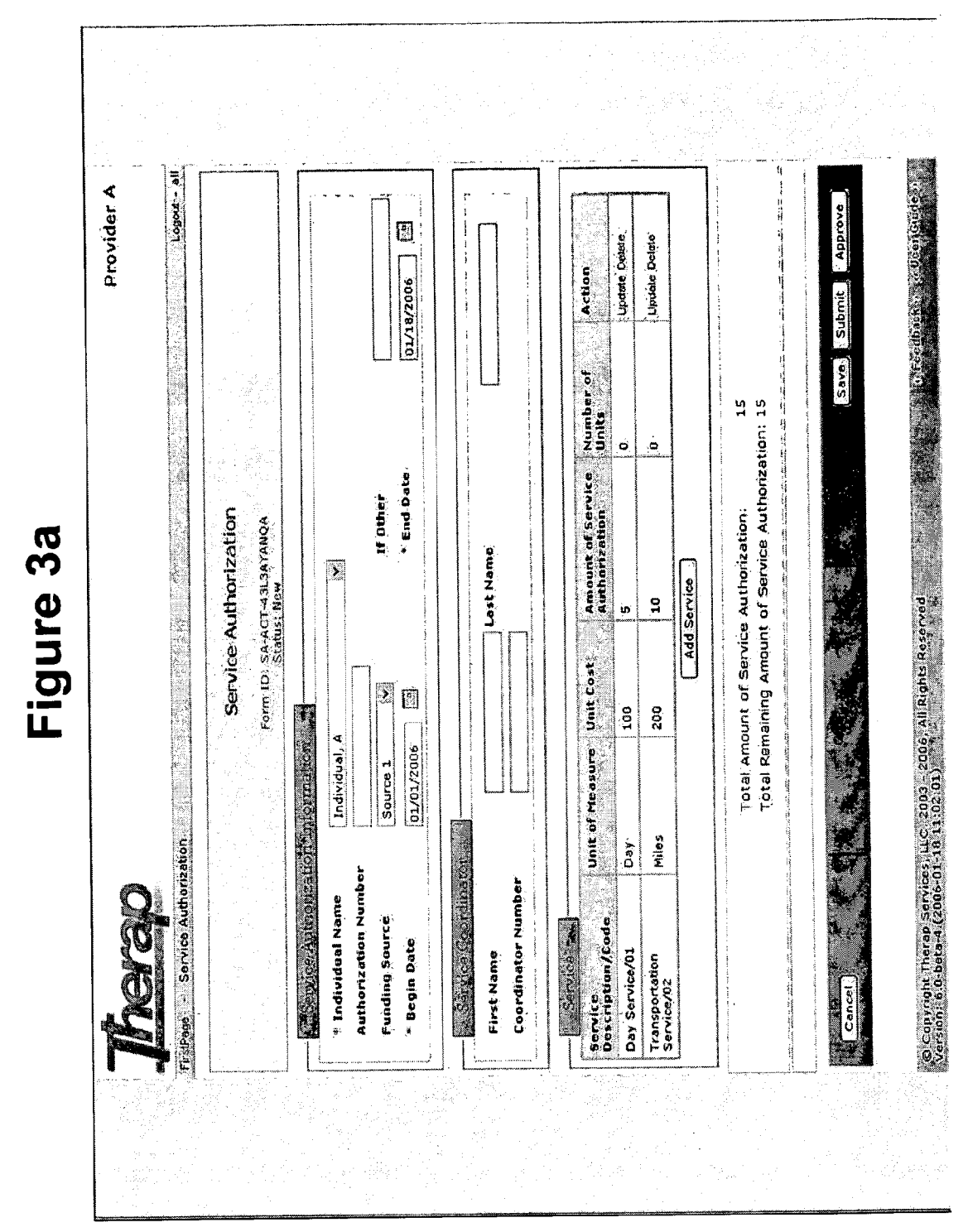

FIG. 3a is a sample of the Service Authorization form requested by an organization such as Security Domain I, an Individual, Parent, or Guardian, Regulators or Funders.

Users with the proper Service Authorization Role are able to log into the system and select a program for which they want the authorization. Selecting the program may take the authorized user to the Service Authorization page, as shown in FIG. 3a. Embodiments of the invention request the authorized user to fill in the appropriate information. A User with appropriate roles may then either Save, Submit, or Approve the authorization. Embodiments of the invention then store the information in a secure database to conform to the privacy and security measures as requested by HIPAA regulations, as well as other laws, regulations, standards, and/or policies.

Figure 4:
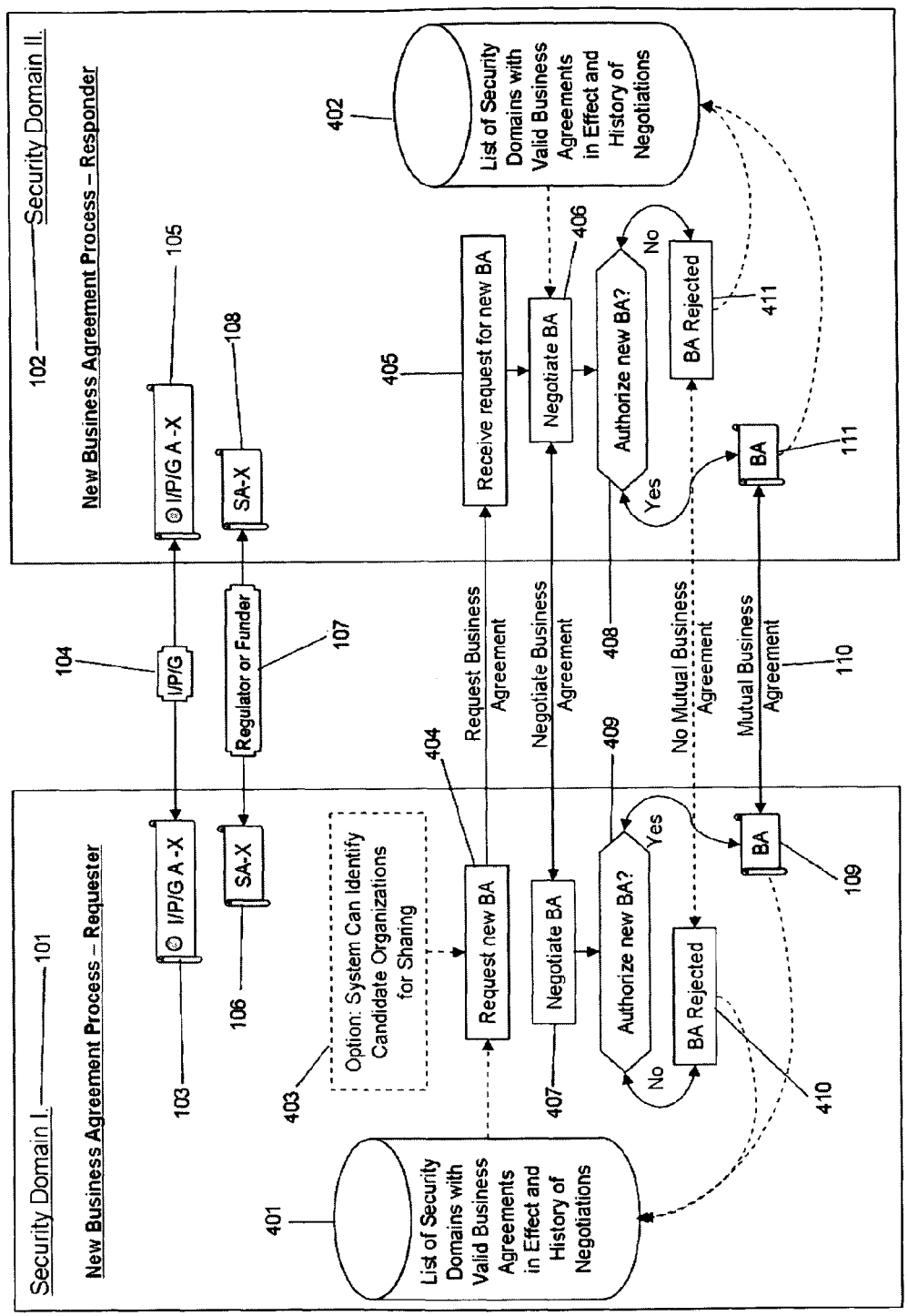
FIG. 4 illustrates embodiments of the Mutual Business Agreement Process.

FIG. 4 shows embodiments of the Mutual Business Agreement Process. This agreement may allow authorized users to securely share private information of Individuals common to different organizations. Thus, embodiments of the invention may allow authorized users to share previous and current information on common Individuals. To initiate such Secure Information Sharing of private information of Individuals common to different organizations, the organizations, representing different security domains, may have a mutual business agreement among them. Embodiments of the invention may function with or without a mutual business agreement; for example, a mutual business agreement may not be executed in a situation where composers enroll in a group which uses embodiments of the invention to share musical information among composers.

Referring to FIG. 4, both the organizations, Security Domain I 101 and Security Domain II 102 are authorized by I/P/G 104 to support Individual X and to share secure information of Individual X between the organizations, I/P/G A-X 103 and I/P/G A-X 411, respectively. The organizations also may be granted Service Authorizations SA-X 106 and SA-X 108, respectively, by the Regulator or Funder (107) before entering a new Business Agreement. Embodiments of the invention maintain the authorization records (401 and 402) for each Security Domain to enforce that sharing is limited to other security domains with which it has valid Business Agreements in effect. The system also maintains a history of previous negotiations on Business Agreements which may be helpful in future negotiations.

Embodiments of the invention allow authorized users, with a Business Agreement Role in one security domain, to initiate a business agreement with another security domain in a secured communications environment. As shown in FIG. 4, Security Domain I 101 (New Business Agreement Requester) requests a new business agreement process with Security Domain II 102 (New Business Agreement Responder) which enables the organizations to share information on common Individuals. Before sending the request, embodiments of the invention may provide a system (403) that allows the organization to identify other organizations which have common Individuals, without revealing the identity of the Individuals, because the system may not allow them to share Private information before the Business Agreement is approved. Security Domain I sends a request for a new Business Agreement (BA) 404 to Security Domain II for a new Business Agreement. This request for a new Business Agreement is received (405) by Security Domain II 102. Embodiments of the invention provide a means of alerting the Responder, who has an appropriate Business Agreement Role in Security Domain II, of the request for a new Business Agreement.

Then Negotiations (406 and 407) between the two Security Domains may occur and so this invention may also provide a mechanism for secure negotiations between the two Security Domains. Upon negotiation of the terms, conditions, organizational policies, and other regulations specified in the requested agreement, the organizations Security Domain I 101 and Security Domain II 102 may mutually accept the Business Agreement (409) or reject it (410). Embodiments of the invention allow the system's users to securely make the negotiations. Embodiments of this invention retain a history of negotiations in a secure database for future reference by Security Domain I 101 and Security Domain II 102.

When the Business Agreement (110) is mutually accepted, embodiments of the invention provide systems which may facilitate sharing of private information of common Individuals ensuring compliance with terms, conditions, and regulations. That is, embodiments of the invention provide systems to assure that information (such as archived or current) are shared if the two organizations have a Business Agreement (BA 109 & BA 111) in effect between them—to satisfy HIPAA requirements or other laws, regulations, standards, and/or policies—and the Security Domains have specifically activated authorized viewing of information by the other. Embodiments of the invention give the organizations greater control over exactly which Individuals are involved, and exactly what roles are permitted for users in one organization to access and use information from the other organization. It also provides the flexibility to manage information flow as requested by HIPAA or other laws, regulations, standards, and/or policies, for example, including tracking the identity and times that users access protected information.

Embodiments of the invention also deal with the situation where one or both organizations terminate the mutual Business Agreement, either explicitly or by going beyond the specified duration of the Business Agreement without renewing it. As soon as the Business Agreement is terminated, sharing between the two organizations may be terminated by the system. Embodiments of this invention may allow for information—for example, information archived before termination—sharing to continue after termination.

Embodiments of the invention allow sharing Individual personal information among different authorized users within an organization or across organizations. It also allows systems to find common Individuals among different organizations. Matching common Individuals may start with having a proper Individual, Parent, and/or Guardian Authorization (I/P/G A), Service Authorization (SA), and a mutual Business Agreement (BA) in effect (if the organization executes such an agreement).

Figure 5:
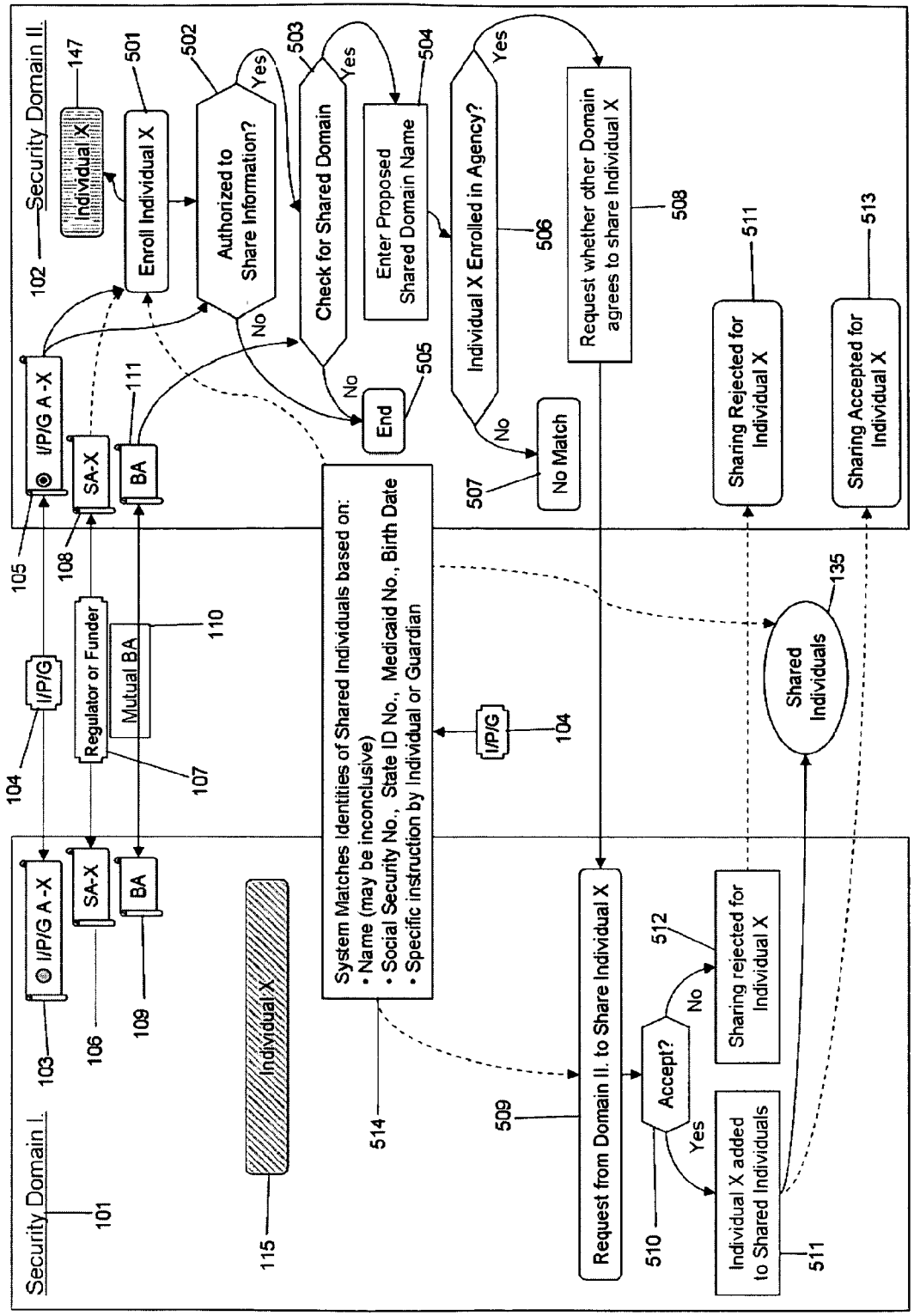
FIG. 5 illustrates embodiments of the system for Matching Common Individual Process.

In FIG. 5, Security Domain I 101 and Security Domain II 102 represent two organizations having a mutual Business Agreement (110) in effect. I/P/G A-X 105 allows Individual X to be enrolled in Security Domain II 102. Individual X is initially enrolled in Security Domain I 101.

While enrolling Individual X in Security Domain II 102 (501), embodiments of this invention may allow authorized users to check (502) if the Individual or Guardian has authorized the organization to share private information of Individual X. If proper authorization is not found, the procedure may end (505). However, when the Individual or Guardian is found to have appropriately authorized private information sharing on Individual X (I/P/G A-X) 105, Individual X can then be enrolled (147). Then embodiments of the invention check (503) to see whether Security Domain II 102 has any mutual Business Agreement(s) 111 with other Security Domains. If the embodiment calls for executing a mutual Business Agreement and no sharing domain exists, then Security Domain II 102 directly enrolls the Individual and no sharing—with respect to that individual's information—occurs. If sharing domains exist, embodiments of the invention provide means to search (503) for particular security domains (for example, Security Domain I 101) with which Security Domain II 102 wants to share information on Individual X. Security Domain II 102 checks (506) if Individual X is enrolled in Security Domain I 101. Embodiments of the invention provide a system (514) for matching the Individuals based on unique identifiers such as Name, Social Security Number, State ID Number, Birth Date and Medicaid Number. If no match is found, the Security Domain II 102 directly enrolls (507) the Individual. If a match is found, embodiments of the invention provide means to send a request (508) to Security Domain I 101 to share information between the two organizations on Individual X.

Today, these matches are typically identified by using a common identification number such as a Jurisdiction specific ID, or a Social Security Number. Although these methods are available in embodiments of the invention, they tend to not work well across Jurisdictions, and Social Security Numbers are not intended for this purpose. Embodiments of the invention provide the unique ability to match across multiple types of information to form a match, even when there are errors in data such as Birth Date, etc.

Embodiments of the invention allow Security Domain I 101 to be alerted when a request is received from Security Domain II 102 on sharing information about Individual X (509). While processing the request, Security Domain I 101 may request the system (514) for matching identities of common Individuals. The request may be processed and Security Domain I 101 may either accept (511) or reject (512) the request to share information on Individual X. Embodiments of the invention also provide the means to automatically accept or reject the request, or to provide for manual intervention. Security Domain II may be alerted of the acceptance or rejection of the request. On acceptance of the request, the two organizations may start sharing information on Individual X (135).

Embodiments of the invention also provide the means to automatically notify Security Domain II 102 that sharing has been accepted for Individual X (513).

Figure 5A:
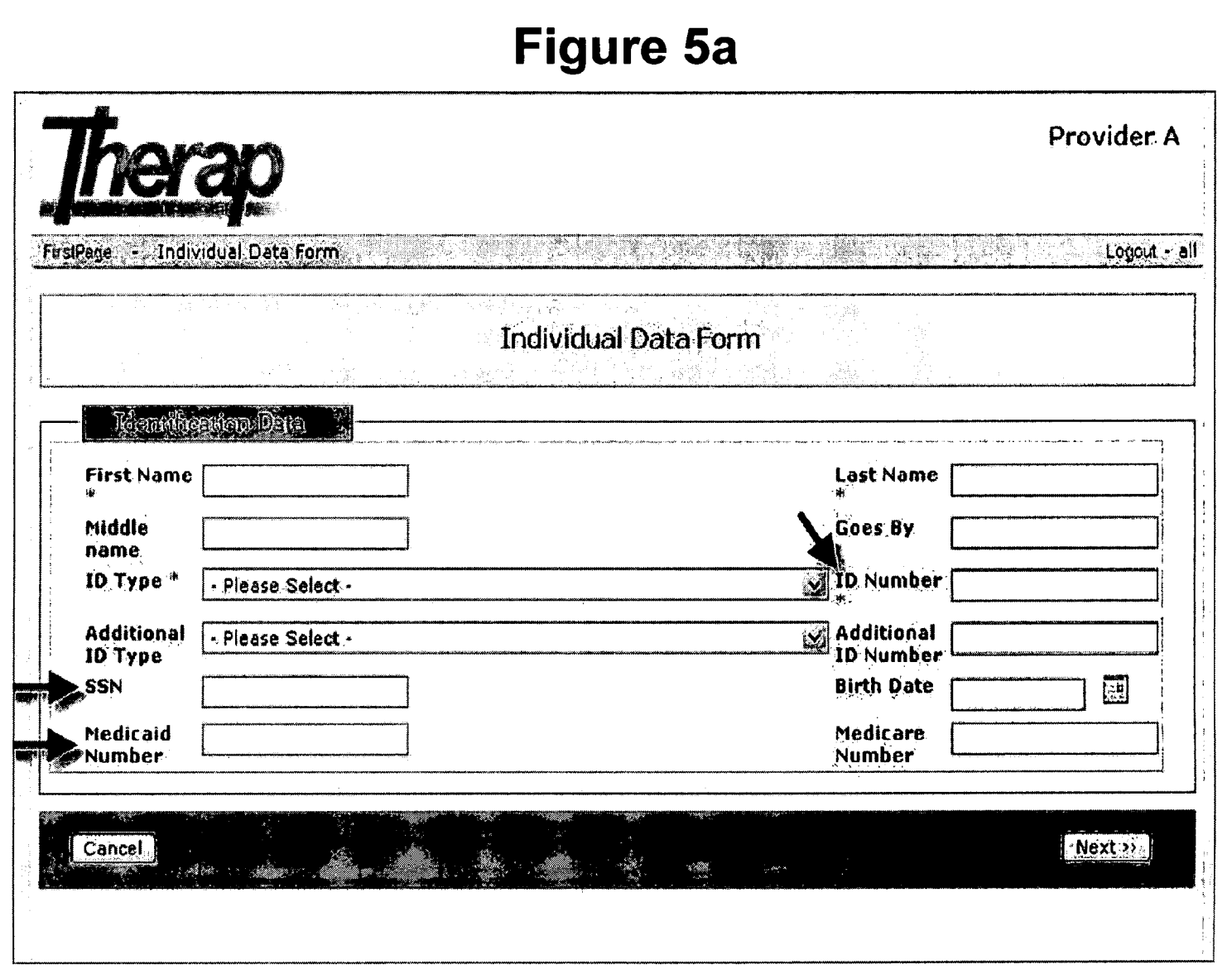

FIG. 5*a* is a sample of the Individual Data Form that requests information which facilitates embodiments of the invention to match shared individuals. Users with appropriate roles log into the system to enroll an Individual via the enrollment process. The enrollment process requests the user to input the Individual Data Form that has been designed to efficiently maintain essential information about individuals the organizations support. As pointed in FIG. 5*a*, it contains information such as ID number, Social Security Number (SSN), Birth Date, and Medicaid Number, all of which may uniquely identify the individuals enrolled. Embodiments of the invention use these identifiers to ensure accuracy in matching Individuals that are/have been requested to be shared among organizations authorized for sharing.

Embodiments of the invention may allow for information sharing by allowing the system to match across multiple types of information. This system may form a match based on names, or other partial information, even when there are errors in data other than the unique identifiers, such as Birth Dates, home addresses, etc. The matching system may be further augmented to allow for minor errors, such as single digit errors, or matching of some numbers are. In the case of severe ambiguity, the user may be asked for more information; however, any request is such that it does not violate, in the case of HIPAA information, the HIPAA privacy rights.

Figure 6:
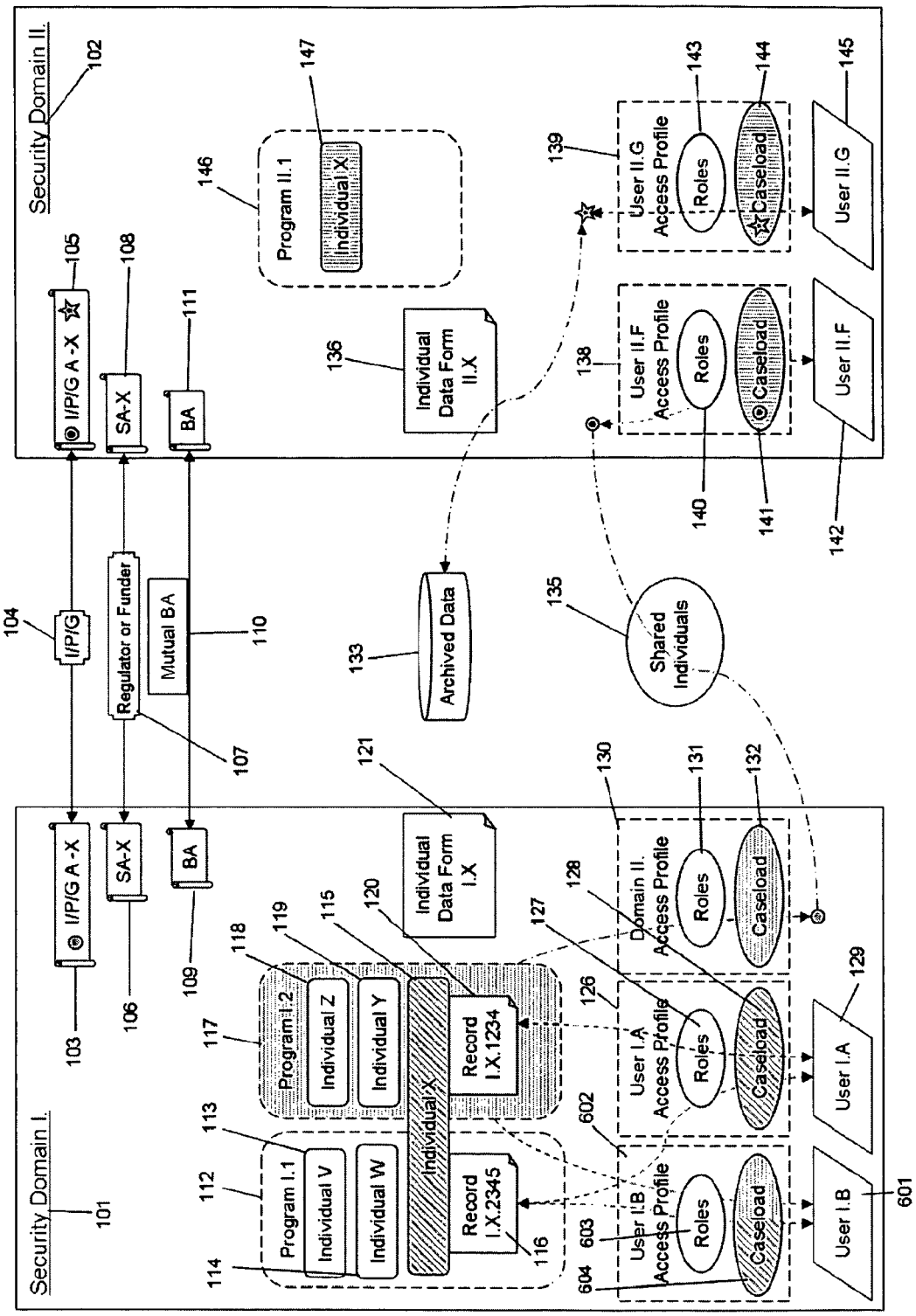
FIG. 6 illustrates embodiments of the system called Caseloads which allows users to share information based on the Individual and how the information was created and stored.

FIG. 6 illustrates the Caseload based security access system. In FIG. 6, Security Domain I 101 and Security Domain II 102 represent two organizations having Individual, Parent, and/or Guardian authorization, Service Authorization granted by the Regulators or Funders, and a mutual Business Agreement in effect. Individual X is enrolled in both the organizations and shared between them.

Referring to FIG. 6, embodiments of this invention may provide systems to define user privileges in flexible ways. Individual X 115, Individual Y 119, and Individual Z 118 are enrolled in Program I.2 117 within the organization Security Domain I 101. Individual X 115 is also enrolled in Program I.1 112 along with Individual V 113 and Individual W 114. Both the organizations 101 and 102 have the required detailed information of Individual X in Individual Data Form I.X 121 within Security Domain I 101 and Individual Data Form II.X 136 in Security Domain II 102.

As shown in FIG. 6, User I.A 129 in Security Domain I 101 has been assigned the Standard Caseload 128 of one Individual in all programs. This may provide User I.A 129 access privileges on Individual X 115. This means that embodiments of the invention may allow User I.A 129 to access records of Individual X 115 irrespective of the programs Individual X 115 is enrolled in. That is, User I.A 129 may access Record I.X.2345 116 in Program I.1 112 and Record I.X.1234 120 in Program I.2 117 of Individual X 115.

Referring to FIG. 6, User I.B 601 has been assigned a Super Caseload 604 (i.e., a set of Standard Caseloads, as indicated by the combination of diagonal and horizontal shading) which provide access privileges on Individual X 115 and Program I.2 117. Embodiments of this invention may allow User I.B 601 to access records of all Individuals (including Individual X 115) in Program I.2 117 and other records of Individual X 115 irrespective of the program Individual X 115 is enrolled in. Thus, User I.B 601 may be able to access Record I.X.2345 116 in Program I.1 112 and Record I.X.1234 120 in Program I.2 117 of Individual X 115.

User II.F 142 in Security Domain II 102 has been assigned the Caseload 141 of one Individual 147 in one Program 603. This may provide User II.F 142 privileges to access information of Individual X 115 in Program II.1 146, as indicated by the "shaded circle". The Access Profile of Domain II 130 in Security Domain I 101 defines privileges for users in Security Domain II 102 to access information of Shared Individuals 135 in Program I.2 117 of Security Domain I 101. Embodiments of the invention have systems to help determine the Shared Individuals among the organizations, for example Individual X 115 and 147 in Security Domains I and II, respectively. Through this system the Access Profile of Domain II 130 in Security Domain I 101 may allow User II.F 142 in Security Domain II 102 to have access privileges on Individual X 115 in Program I.2 117 in Security Domain I 101. Thus, User II.F 142 in Security Domain II 102 may have access to Record I.X.1234 120 in Program I.2 117 in Security Domain I 101 of Individual X 115, but not record I.X1234 120.

With the Access profile of User II.G 139 in Security Domain II 102, embodiments of this invention may allow the user to have access privileges on the archived data 133 of Individual X 115 and 147.

Figure 6A:
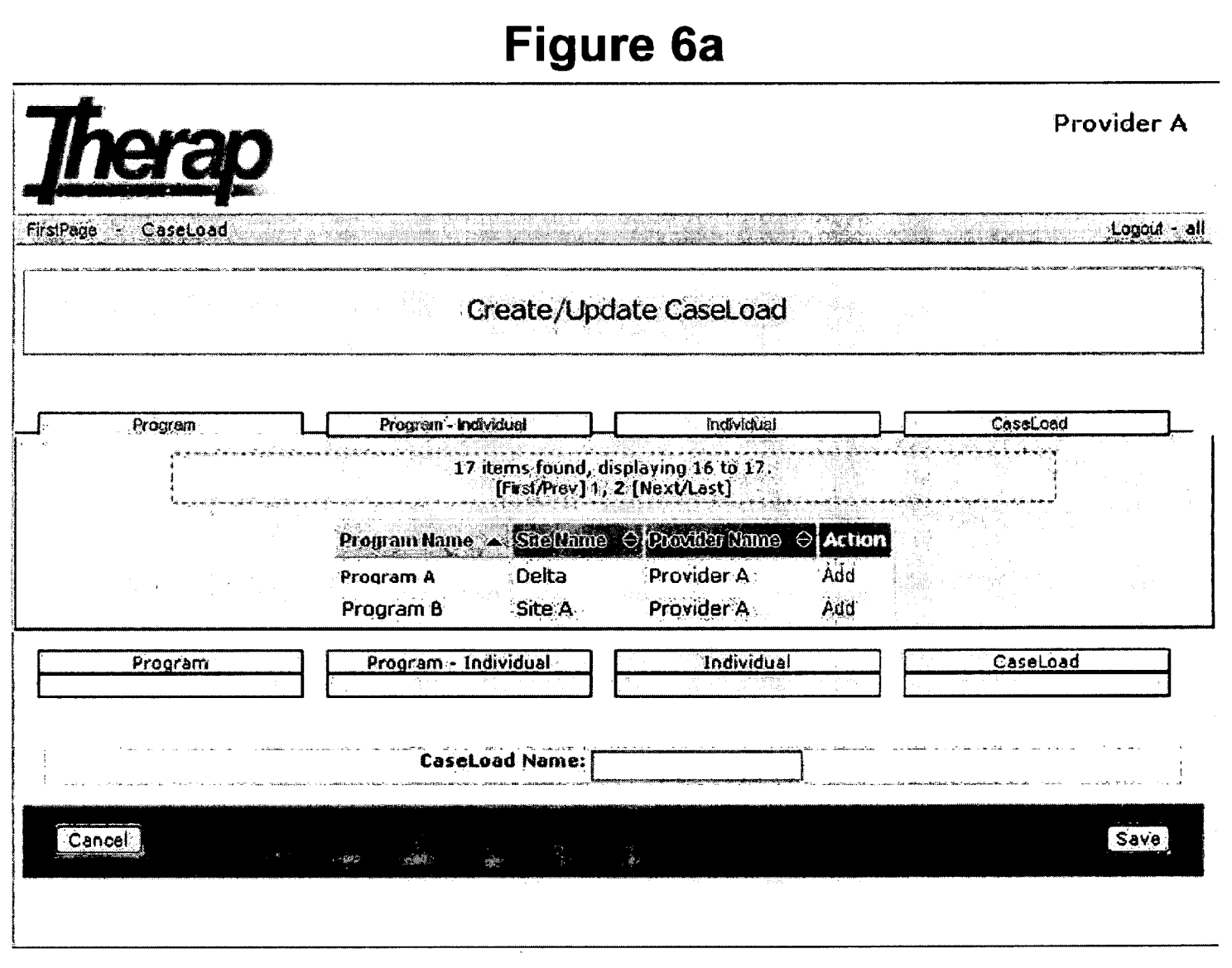

FIG. 6*a* is a sample of a screenshot where the users are assigned Caseloads to match their authorizations. A User with the appropriate role may log into the system and select the Caseload to be created. For example, if Standard Caseloads on a program are to be assigned, the authorized user may select the particular Program (from the list of Programs provided in the page) to which the Caseload is to be added and then provide a Caseload Name. Clicking on Save may create the Caseload and thus it may be saved in the system.

Caseloads specify which Individuals and which Programs a user is allowed to access information about. The actions a user is allowed to perform on that information in an embodiment of the system is specified by Security Access Roles, or just Roles.

Figure 7:
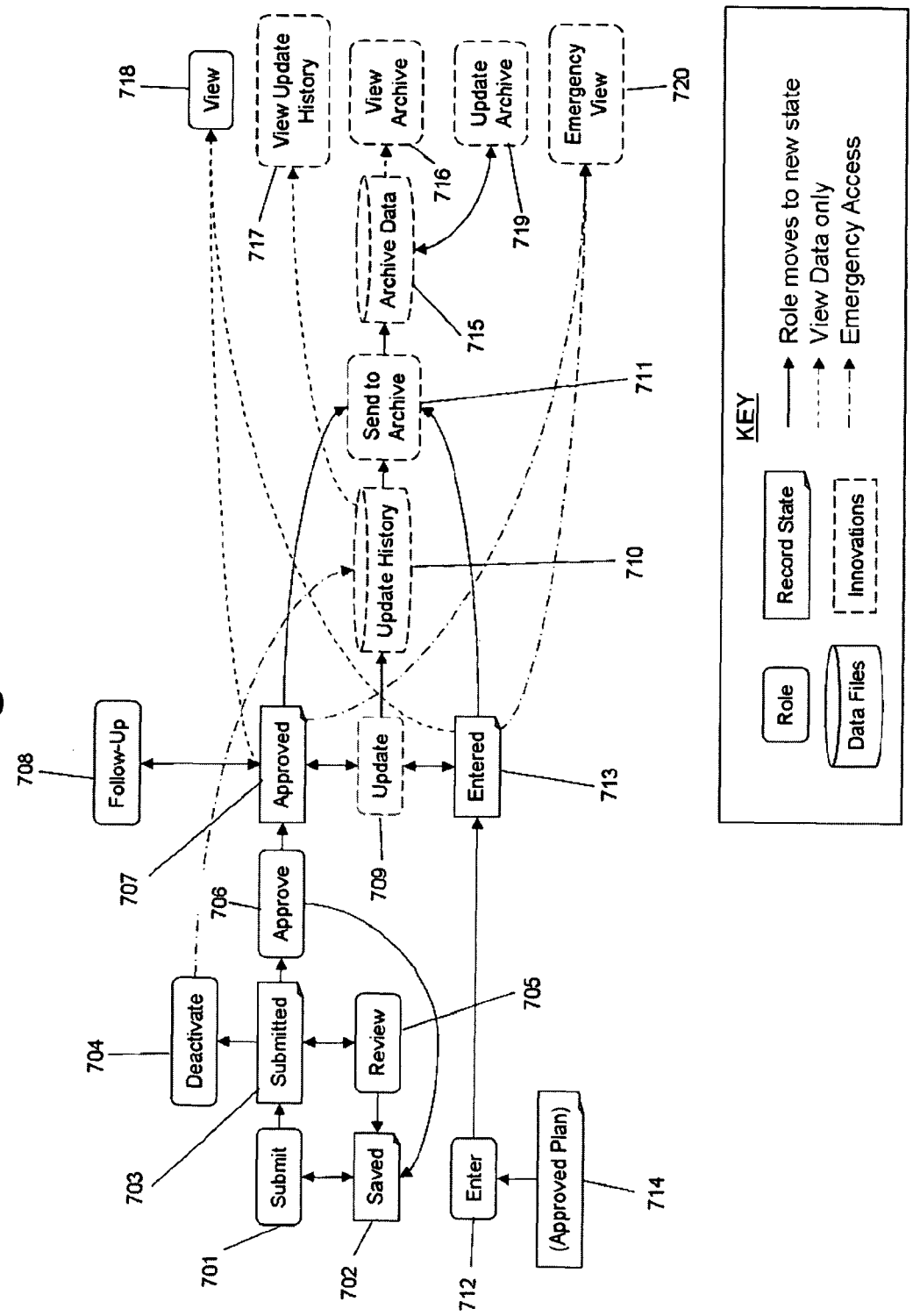
FIG. 7 illustrates Security Access Roles which define the actions users may perform on Individual information.

FIG. 7 shows a schematic diagram of the basic functions and relationships of Security Access Roles. The Roles determine the functions a user is permitted to perform on specified types of information about an Individual.

For ease of explanation, Roles are grouped into three types: those that apply to "plan" or "report" applications, those that apply to "data" applications, and those which may be common among the applications. Examples of "plan" or "report" applications are: Individual Data Form that holds detailed personal information of an Individual, Event Reports which record different critical and sensitive information on events that have taken place with an Individual, Behavior Plan, which illustrates a set of behaviors an Individual is likely to display, and Individual Support Plan, that is used to teach an Individual different tasks and record progress. Examples of "data" applications are: Secure Communications to send different types of secure electronic messages to users in a secure way, T-Log to inform other authorized users of different issues in the organization, Health Tracking to record different health information of Individuals, Behavior Event (optionally based on the corresponding Behavior Plan) and ISP Data based on a session as described in the Individual Support Plan. Roles are assigned separately for each application to assure that the user only has access to the types of information and specific actions which are appropriate for their job functions.

The Roles which may apply to "plan" or "report" applications are: Submit 701, Review 705, Deactivate 704, Approve 706, and Follow-Up 708. A user with a Submit Role 701 may enter new data, and then either Submit it for Approval or temporarily Save 702 it for further work. A user with a Review Role 705 may add Review comments, or return the plan to the submitter for further work. A user with the Approve Role 706 may modify the submitted 703 plan, Approve it, or Return it to the submitter for further work. A user with the Deactivate Role 704 may take a submitted plan 703 mark it as deactivated and that plan will be placed in the Update History 710 and no longer show as a submitted plan 703. A user with the Follow-Up Role 708 may end follow-up comments to approved plans 707.

The Role which may apply to "data" applications is: Enter 712. The system allows an authorized user with Enter Role 712 to enter such information that requires no approval. Such information is referred to as the Approved plans 714 as soon as they are entered.

The Roles which may be applied to either type of application are: View 718, Update 709, Send to Archive 711, View Update History 717, View Archive 716, Update Archive 719, and Emergency View 720. A user with the Update Role 709 may make a change to an Entered 713 or Approved 707 record; the old version is stored in Update History 710, along with the time and date of the change and the name and title of the user. In addition to Updates described above, information may be sent to the Archive 715 when (1) an Individual is enrolled in an organization for prolonged period, the old information is sent to archive to efficiently manage all relevant information; or (2) any Individual leaves the organization, embodiments of the invention allow storing of the individual's information in an Archive 715. A user with the Send to Archive Role 711 may move data from the Approved 707 or Entered 713 states into the Archived state so that it is no longer available to the non-Archive Roles. A user with the View Update History Role 717 may view corresponding information in the Update History 710. A user with View Archive Role 716 may view and retrieve information from the Archive Data 715. A user with Update Archive Role 719 may make updates to the archived data; the old version is stored in Archived Data 715, along with the time and date of the change and the name and title of the user. A user having limited access to an Individual's information may be given an extended authorization, e.g. Emergency View role 720, to access that information depending on the degree of emergency.

Referring to FIG. 7, the flow of information across each state can be described as follows: Authorized users may enter information on the Individual and save the information for further modifications. The system may ensure security by allowing such authorized users to save, submit, and review information on Individuals. As shown in FIG. 7, the information recorded on Individual may be entered and saved 702. If a record has been saved 702, it may allow the originator to access and modify it. If a record is submitted it moves to Submitted state 703 where it awaits for approval. Embodiments of this invention have systems to ensure that users with the Review 705/Approve 708 role are alerted when a report is waiting for approval. The user with the Approve role 708 may then review the information and make necessary changes. After reviewing, the information may again be saved and submitted for approval, or be directly approved by the approver.

Users with appropriate authorizations e.g. having a Deactivate role 704 may also deactivate the submitted information if requested. Embodiments of the invention allow such information to be stored in a secure database 710 for users with proper roles to access the information.

Embodiments of the invention provide systems to store approved (707) Individual information in a secure database 710 and to retrieve and view those information for further analysis or use.

Figure 7A:
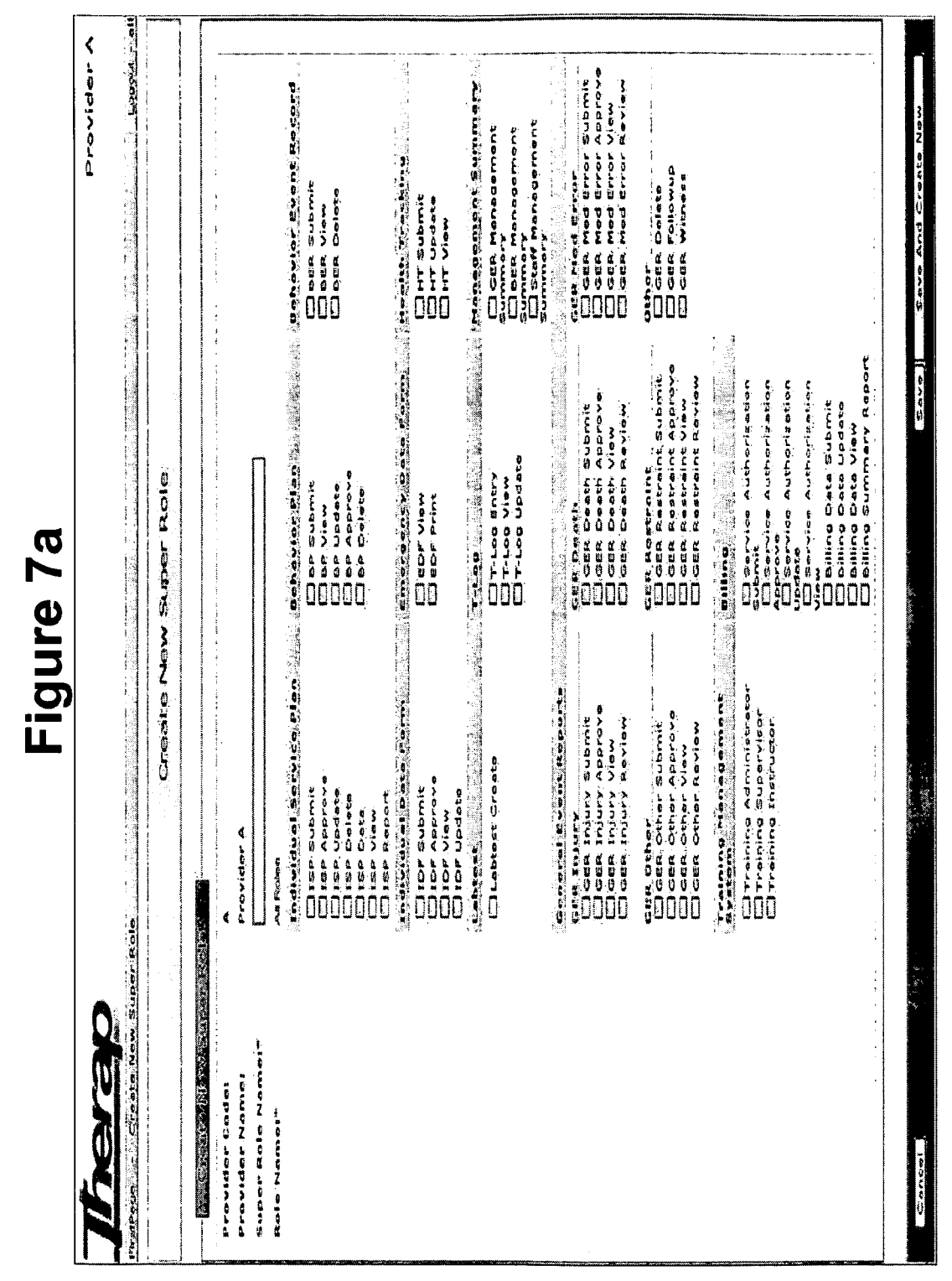

FIG. 7*a* is a sample of a screen shot which allows Roles to be grouped into a Super Role that may be assigned to users. A Super Role is a standardized job classification or position. The figure shows the roles which are applied to particular applications in this embodiment of the system.

Figure 8:
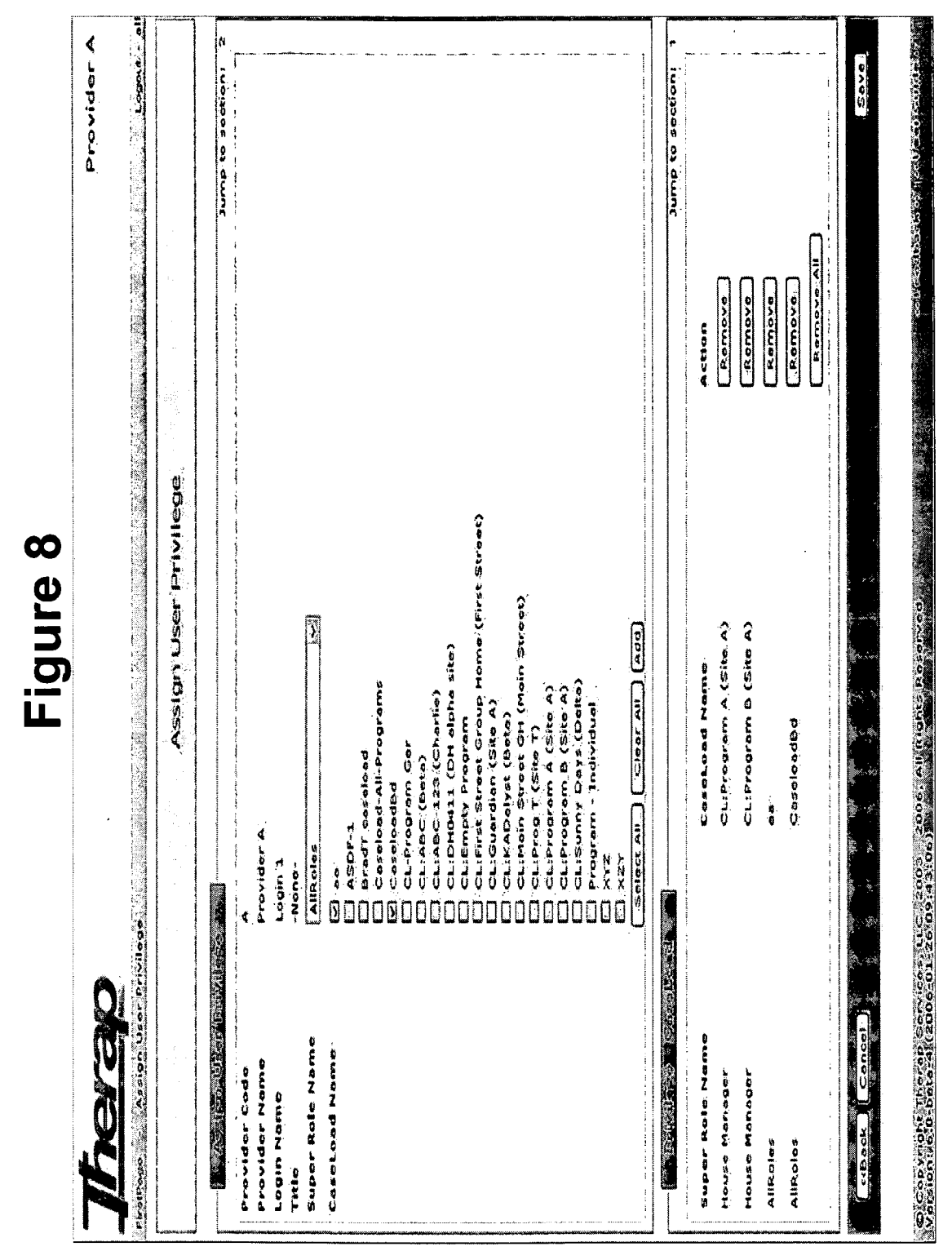

FIG. 8 is a sample of a screen shot where embodiments of the invention allow a user with suitable authorization, a Data Administrator, for example, to assign Super Roles and Caseloads to an authorized user to access the Therap System and may be created by combining one or more of the Roles provided by the system, to enable the authorized users to securely and adequately perform their tasks. A Data Administrator may be authorized to create accounts for other appropriate users and assign roles and/or Super Roles to them. Once the Super Role is created, it is assigned by the Data Administrator to the authorized users. This assignment process requests the Data Administrator to click on the User Privilege link on FirstPage, select an authorized user from the list available and then reach the Assign User Privilege page. The Data Administrator then selects and assigns the Caseloads to the user. The bottom section of the Assign User Privilege page provides a record of the Super Role Name and Caseload Name that had already been assigned to the user. Thus, embodiments of the invention provide a system that allows assigning access privileges securely based on different combinations of Individuals, security domains, and other Caseloads, which streamlines the process for the authorized users to get privileges based on their preferences and needs. Also, authorized users may remove specific privileges for a user if the authorizations change.

Requirements for an implementation which embodies the invention generally include resistance to failures in hardware, software and operations, and other aspects of the system to ensure against the loss of data, as well as to provide a very high probability of being able to access the data at any time. To accomplish these objectives components of the system are replicated in proportion to their likelihood of failure.

Figure 9:
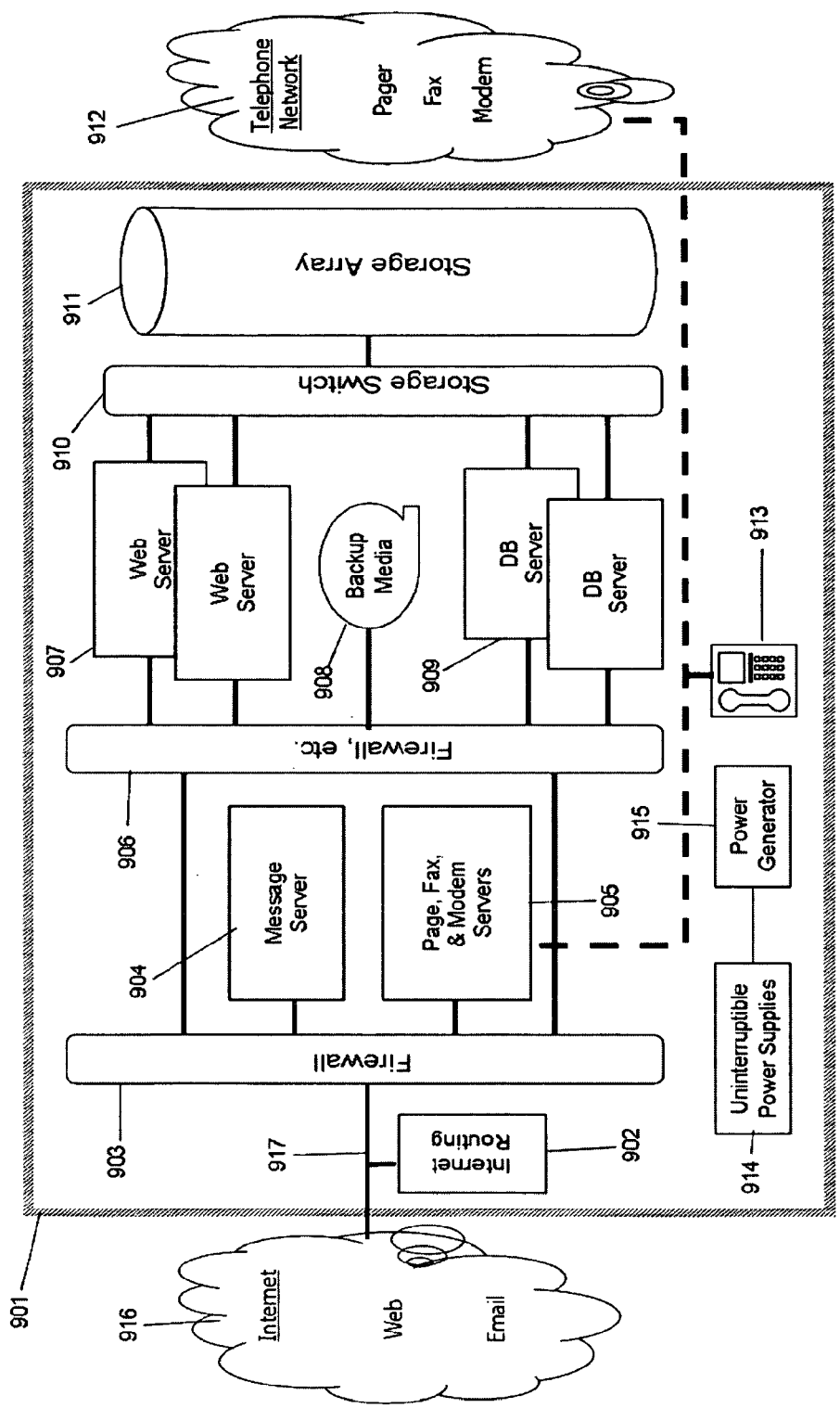
FIG. 9 illustrates a Sample Physical Architecture for running an embodiment of the invention.

FIG. 9 is a high-level overview of a sample of an implementation which could run an embodiment of the invention. The node 901 is connected to the Internet 916 by one or more high-speed connections 917 to provide reliable access. Individual Internet connections 917 are relatively unreliable, and thus Internet routing technology 902 provides the ability to automatically switch from one Internet access to another so that users do not experience a failure in accessing the system because of a failure in the Internet connection 917.

The Internet 916 unfortunately allows many unwanted access opportunities, and thus a set of firewalls 903, 906 are used to screen unwanted access. One aspect of providing communications is the ability to send or receive messages of various kinds over the Internet and thus a message server 904 is required; this is software running on a computing platform. Other types of messages are sent and or received via pagers, fax, and modems; to implement these additional servers 905 are used, and these also connect to the telephone network 912.

The remaining servers need to be further protected from harmful Internet traffic and thus another set of firewalls 906 and other protections are used.

The service is implemented using secure Web access, and thus Web servers 907 are employed. Both because they are critical to providing the services described in the invention, and also to provide capacity for high loads, multiple Web servers 907 are employed. Part of the function of the firewalls, etc. 906 is to distribute the traffic to the appropriate servers 907, 909.

Another key aspect of implementing the system is the database server 909. Similar to the Web servers 907, the database servers 909 are replicated for reliability and capacity.

The most likely single failure in the hardware is a disk drive, so a storage array 911 is employed. A storage array 911 contains a large number of physical disk drives with several methods of replicating the data across the individual drives. The combination of the storage switch 910 and the storage array 911 assures that the Web servers 907 and the database servers 909 can gain access to the data when needed. A storage array 911 is designed for operation and even replacement of failed disk drives and other components, such as power supplies and disk controllers while the storage array 911 is still operating, providing seamless access to the data.

As part of the operations, especially in the case of emergency, waste medications needs to be provided and thus there are telephones 913 connected to the telephone network 912 including wired and wireless communications.

None of the systems can operate without electoral power, and thus uninterruptible power supplies 914 are used. These are basically batteries with control circuits so they can immediately take over in the case of loss or reduction in the electoral power. In the case of extended power outage the uninterruptible power supplies 914 would not be able to maintain power indefinitely, and thus a power generator 915 is also included in the design.

Taken together these provide a very reliable platform for operating the software to implement an embodiment of the invention. However, there is still a possibility of a catastrophic failure, such as a major fire, and thus the data need to be stored elsewhere. One redundancy mechanism is periodic for example daily, backup of the data to backup media 908.

Figure 10:
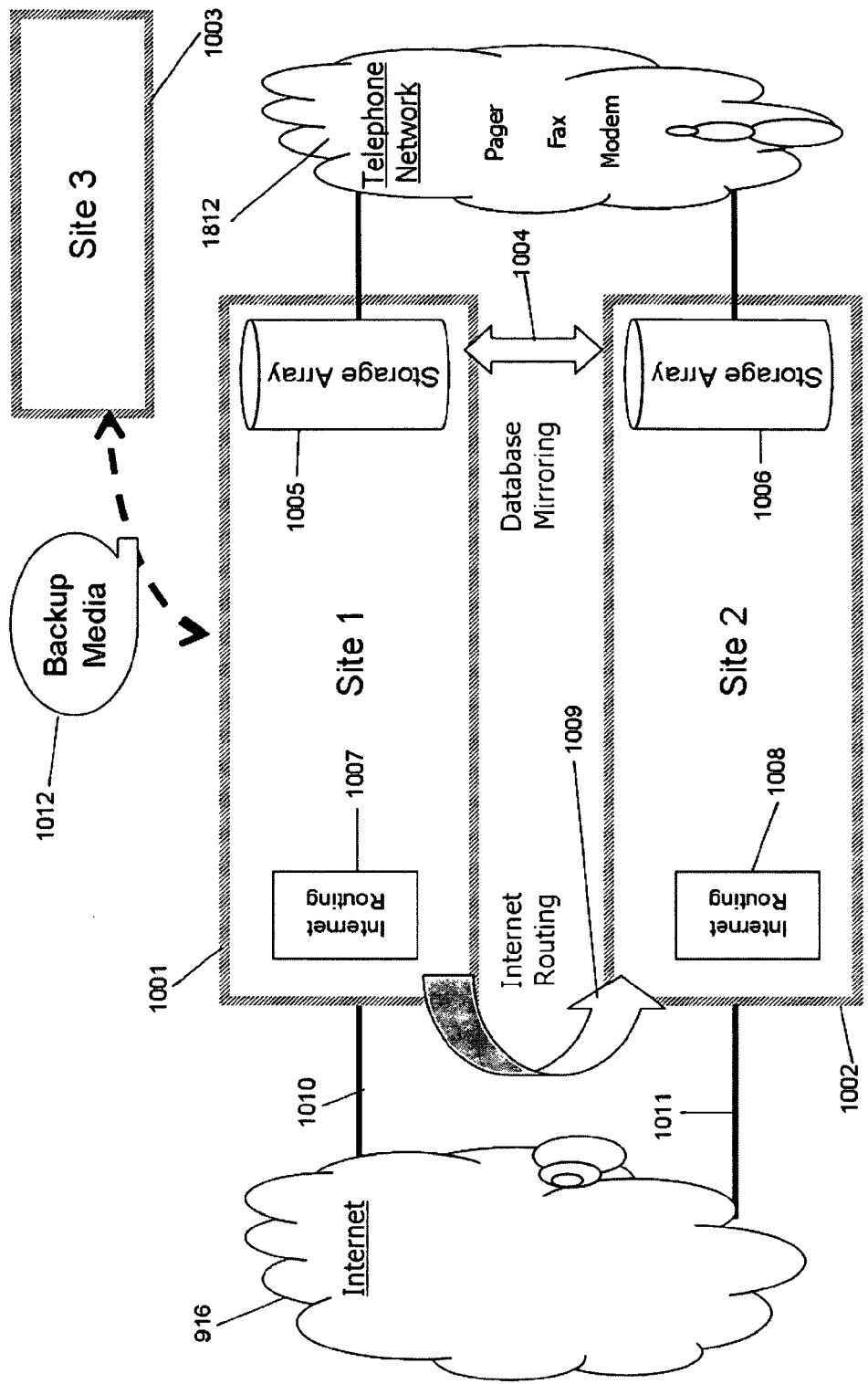
FIG. 10 illustrates a Sample Physical Architecture for Redundancy Operations for running an embodiment of the invention.

FIG. 10 is a sample how redundancy across different physical locations can be used to increase the reliability of an embodiment of the invention.

For example a physical node 901 as shown in FIG. 9 could be implemented at Site 1 1001 and also at Site 2 1002.

Special software and operations 1004 are employed so that the data in the storage array 1005 at Site 1 1001 and the storage array 1006 at Site 2 1002 are continuously synchronized or "mirrored". For example, a user may enter data into the embodiment of the invention running on the node at Site 1 1001. Almost immediately the data is copied to the storage array 1006 at Site 2 1002.

Now assume that there is a failure of some sort so that traffic is not able to access Site 1 1001. This could be due to any number of reasons, including the failure of the Internet access links 1010, or failure of critical hardware or software at the node at Site 1 1001.

The system detects this failure and uses the Internet routing capability 1009, using the Internet routing components 1007, 1008. Internet traffic is now automatically routed over the Internet access 1011 to Site 2 1002. Because the data are already available in the storage array 1006 at Site 2 1002 the user does not notice that any sort of failure has taken place.

As a further caution against him multiple disasters, the backup media 1012, which are recorded created, are stored at it a different site 1003. In the case of catastrophic failure, the database could be restored to the point of the last backup from the fact that media 1012.

Taken together these types of taken techniques provide a very high likelihood of not losing data permanently and of being able to access and use the data at any instant.

This type of distributed implementation can be used in several different ways. More than two nodes can be employed to provide higher capacity and higher reliability and availability. The physical and software implementations at different nodes do not need to be identical as they are relatively independent; the only requirements are that the Internet routing capability 1009 and the database mirroring 1004 can operate among the nodes. Thus it is possible for any node implementing an embodiment of the invention to be a very simple device, such as a single computer with some associated equipment. And that implementation could work with other implementations, such as that shown in FIG. 9. It is also possible that the nodes can be operated in widely separated geographical areas, and even in different nations, as long as the Internet routing capability 1009 and the database mirroring 1004 can operate successfully over long-distance, the delays in synchronization between the two databases 1005, 1006 may be delayed, but this can be accounted for in the operation of the overall system. Further, it is possible to have traffic from some users preferentially routed to one node 1001, while other users are actually routed to another node 1002 and still have the nodes backing up the overall database.

Thus the implementations described provide a very flexible mechanism for embodiments of the invention.

Figure 11:
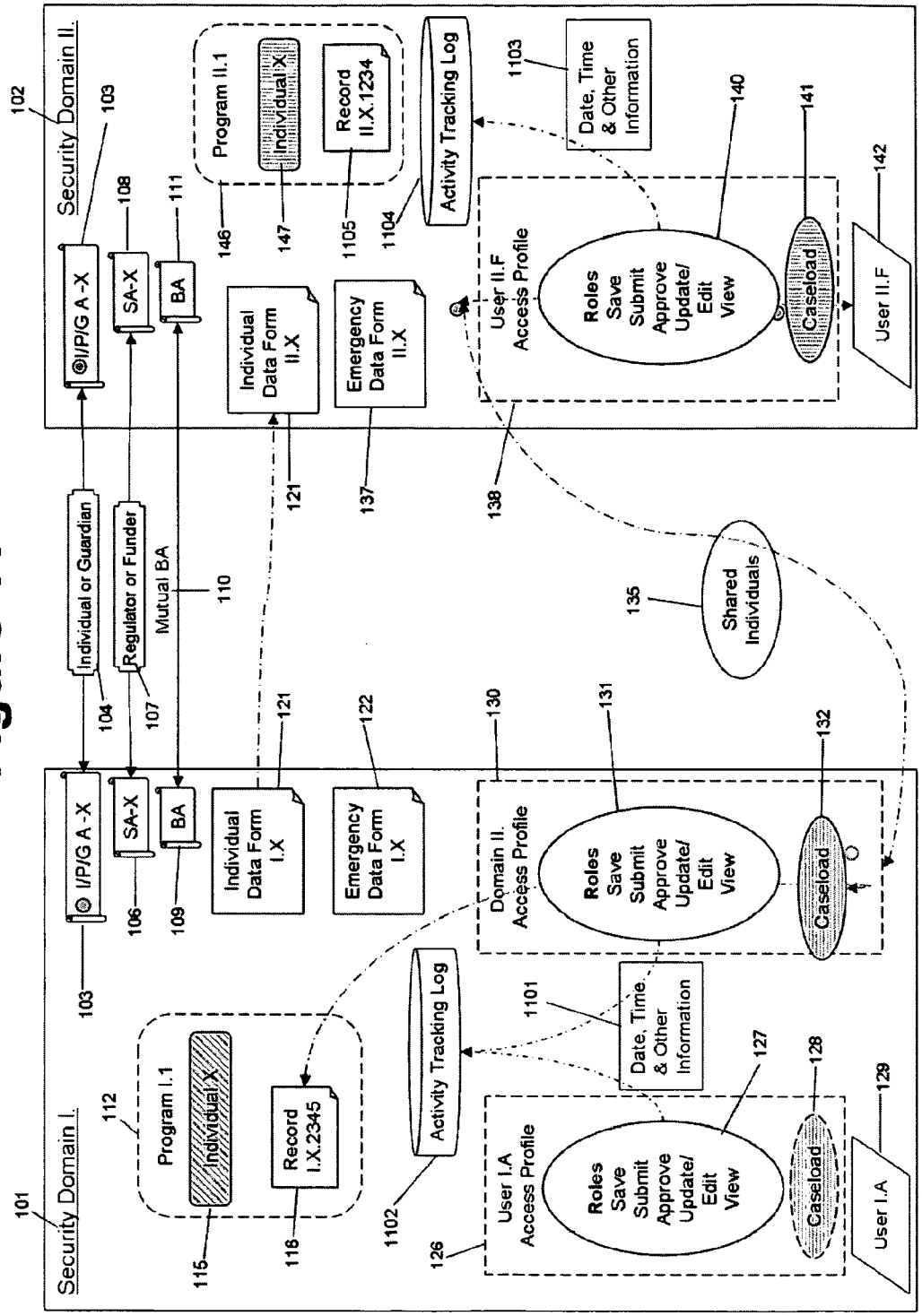
FIG. 11 illustrates the embodiments of the system which allow Tracking Activity across Security Domains.

FIG. 11 is an overview of the system that allows Tracking Changes in Information among Security Domains. Embodiments of the invention may provide systems that allow follow up of the changes brought about in the information being shared among the organizations.

In FIG. 11, Security Domain I 101 and Security Domain II 102 represent two organizations having Mutual Business Agreement 110 (Mutual BA) in effect. Both the organizations are authorized by the Individual, Parent, and/or Guardian 104 to support and share Individual X 115, enrolled in both organizations, among them. Security Domain I 101 and Security Domain II 102 also have Service Authorizations (SA-X) 106 and 108 granted by the Regulator or Funder 107 for Individual X 115.

Security Domain I 101 has Access Profile of Domain II 130 which includes a set of roles 131 that defines the extent of privileges a user in Security Domain II 102 may hold to access and share information on common Individuals 135 enrolled in both the organizations. Each time a user (either User I.A or User II.F) exercises a role depending on his/her access privileges defined in the caseloads 128, 132 and 141, that activity is described in an Activity Tracking Log 1102, 1104. Specifically the date and time, the roles, the information accessed, and various information, referred to by I 101 and 1103, about the user are recorded in an Activity Tracking Log 1102 in Security Domain I 101 and 1104 in Security Domain II 102.

To maintain the consistency of information on shared common Individuals in both the organizations (Security Domain I 101 and Security Domain II 102), embodiments of the invention allow systems to store the information securely and restrict its access. The information recorded may be characterized as Confidential and Restricted.

For example, the Individual Data Form I.X 121 in Security Domain I 101 comprises of detailed personal information on Individual X 115. It may also contain information that may be essential in special emergency situations to Security Domain I 101, but may not associate to an Individual directly. Such information is considered and thus marked confidential because it may differ according to each organization's requirement, which may depend on the internal operations of the organizations. Thus, embodiments of the invention allow the information to be stored and shared in a secure environment to maintain the privacy and accountability guidelines of HIPAA, as well as other laws, regulations, standards, and/or policies. The information that are marked Restricted comprises of extremely sensitive and confidential information. Embodiments of the invention ensure that access to view or modify such information is available to authorized users. Through the Shared Access Profile the invention thus provides systems to securely View and/or Update record on the common Individual information. Embodiments of the invention thus provide this security by keeping track of every detail of actions performed on any data. Any access to the system or any action performed is logged noting User ID, time, date, data ID, and activity FIG. 11a is a sample screenshot of the records saved securely to facilitate Tracking Changes in Information within and among Security Domains due to different users' activities. The records include User Login Name, Internet Protocol (IP) address—which is a unique number used by computers to refer to each other when sending information through the Internet (note that with some types of Internet access, the IP address of a computer may change from one session to another), Activity Type—which is the activity performed on information, Module Name—which is the name of the application being used, Action, Form ID—which is Identification Number of the form, Date and Time of the user's activity, Program—which is the service classification where information has been changed, and Comments. Authorized users may access the Activity Tracking Log. Embodiments of the invention may allow users from different organizations—which have appropriate agreements in effect—to share and access this information.

Figure 12:
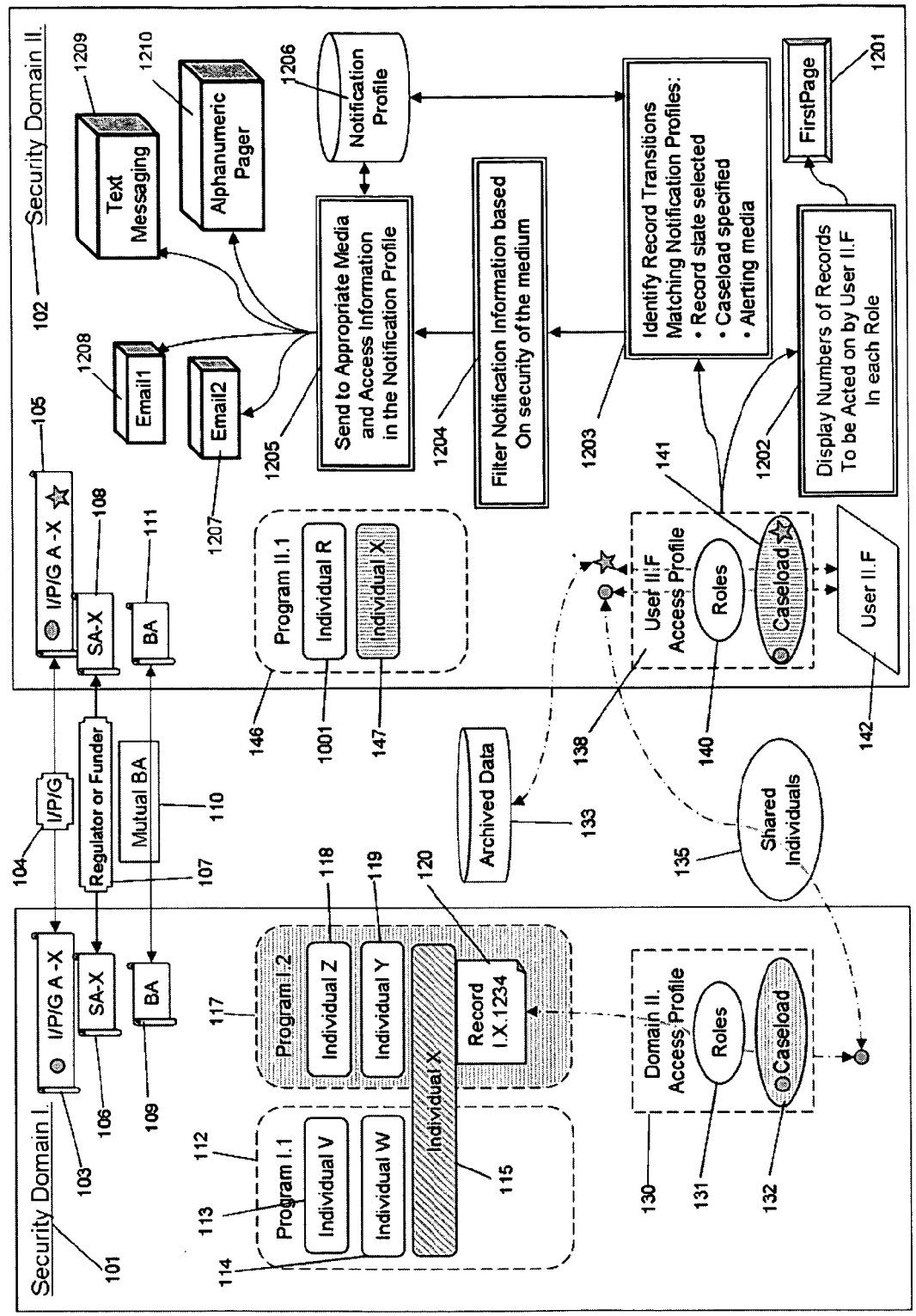
FIG. 12 illustrates embodiments of the Notification System which notifies or alerts users to changes in Individual information through secure and non-secure notification media.

FIG. 12 illustrates embodiments of the Notification System through which embodiments of the invention alert the users of specific events within the system for which they are authorized to have access.

In FIG. 12, Security Domain I 101 and Security Domain II 102 represent two organizations having Mutual Business Agreement 110 in effect. An Individual X 115 is enrolled in both the organizations. This means that both Security Domain I 101 and Security Domain II 102 are authorized by the Individual, Parent, and/or Guardian 104 to support and share Individual X 115 among them. The organizations also have Service Authorizations 106 and 108 granted by the Regulator or Funder 107 for Individual X 115.

Referring to FIG. 12, embodiments of the invention provide a system which alerts the users of the actions they wish to perform on Individual information. Such an embodiment of this invention is the screen users see when they log on to the system ("FirstPage") 1201. This interactive page may inform the users of what information is available for them and permits them to select reports they wish to work on. This means that as soon as User II.F 142 logs in, the number of records 1202 to be acted on by User II.F 142 defined in each of the roles in User II.F Access Profile 138 is displayed in User II.F's 142 FirstPage 1201. FirstPage 1201 personalizes itself for each user. It lists all reports waiting for the user to view or work on based on their authorized access to each application, and the information on Individuals for which they are authorized in the corresponding caseload. Note that FirstPage is secure because it is only available after the user has log into the system, and only shows information and actions for which that specific user is authorized.

Notification may also be performed through other media. Embodiments of this invention allow for users to configure their Notification Profile 1206 to meet their specific needs. This facilitates information sharing by ensuring that the authorized users are appropriately notified when certain actions have been performed on information of Individuals for which the user is authorized. Embodiments of this invention may allow each authorized user to personalize their notification profile according to their specific needs. This system is available on FirstPage 1201 for every valid user, although it may be limited by the Data Administrator, and a default notification profile may be specified by the Data Administrator for each Super Role.

As shown in FIG. 12, the Notification Profile system 1206 comprises options that let the users select their own preferred way of receiving alerts. Embodiments of the invention allow users to choose the media 1205 through which the user wants to be alerted. Some of these media are not secure, so embodiments of the filter the information to assure that no private information is sent over a non-secure media 1204; thus non-secure media may receive only limited information compared with what is sent over a secure medium. For example, the name of an Individual cannot be sent over a non-secure medium. The media available for alerting the users are, for example, Electronic Mail 1207 and 1208, Text messaging 1209 and/or Alphanumeric Pager 1210. The users may also select the programs they want to be alerted of, as soon as relevant information has been recorded. Users may be alerted of different actions (such as Submit, Approve, Delete, Return, Review, and Follow-up) that are performed on reports of Individuals in the chosen programs. The users may also be alerted based on different degrees of notification level.

Figure 12A:
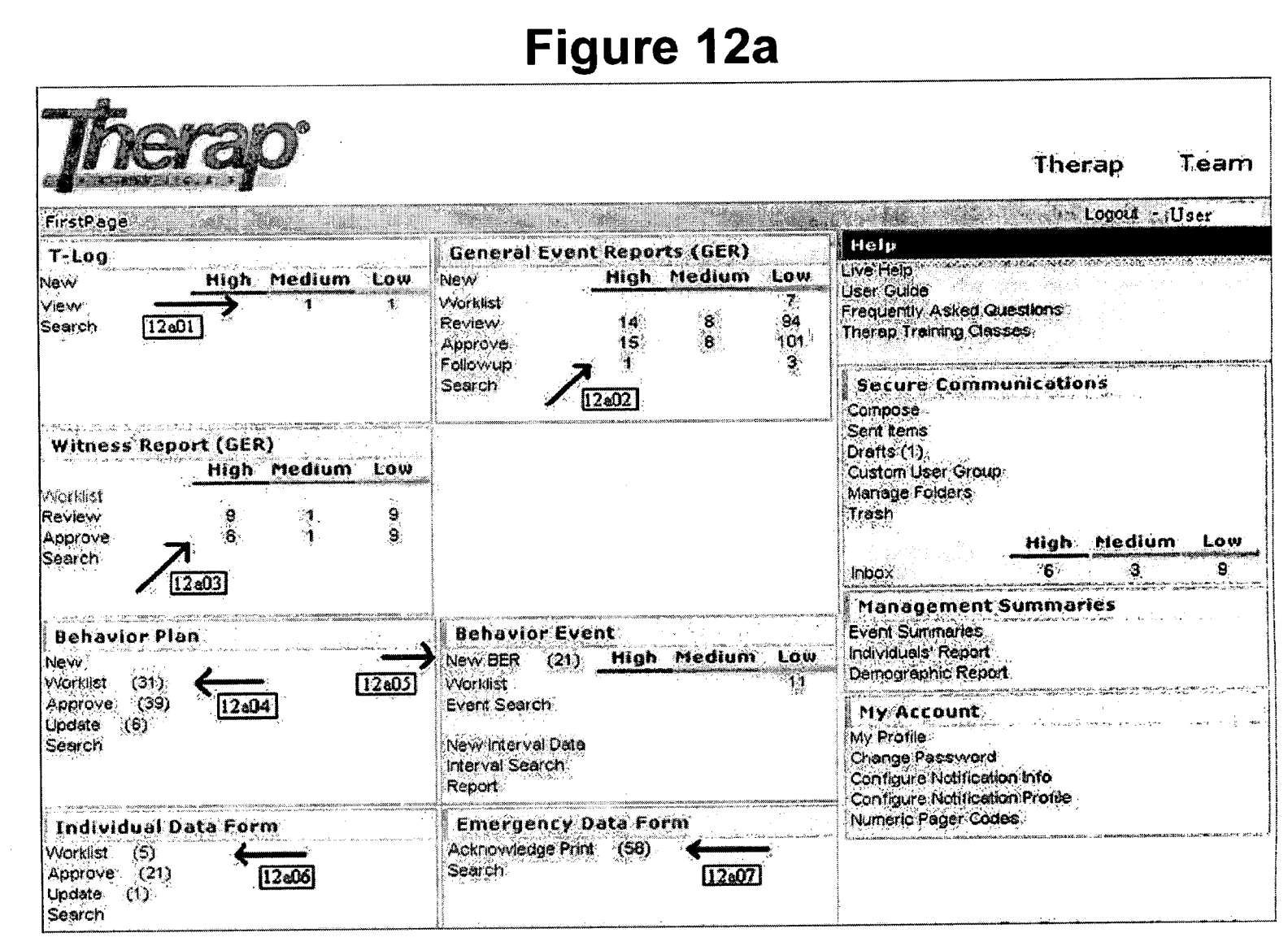

Embodiments of this invention provide systems to identify users who specified to receive notifications of the performed action when certain actions have been performed 1203. The Notifications are sent via the media the user has specified in the user's Notification Profile. Embodiments of this invention may also provide systems which ensure that appropriate users are alerted of their actions on time and such messages are secure and not malicious 1204. Embodiments of the invention may prevent inappropriate information from being sent across non-secure media. FIG. 12*a* is a screenshot of the FirstPage. This diagram illustrates the scenario of how an authorized user receives notification as soon as s/he enters the secure system. The arrow 12*a*01 indicates the number of tasks with level of emergency the user needs to View under the module 'T-Log'. Similarly the arrows 12*a*02, 12*a*03, 12*a*04, 12*a*05, 12*a*06 and 12*a*07 indicate numbers that specify the number of forms and/or reports on which an authorized user is required to perform his/her authorized actions. Since FirstPage personalizes itself for each user, the number of reports waiting for the user to work on is based on their authorized access to each application, and the information on Individuals for which they are authorized in the corresponding caseload.

Figure 12B:
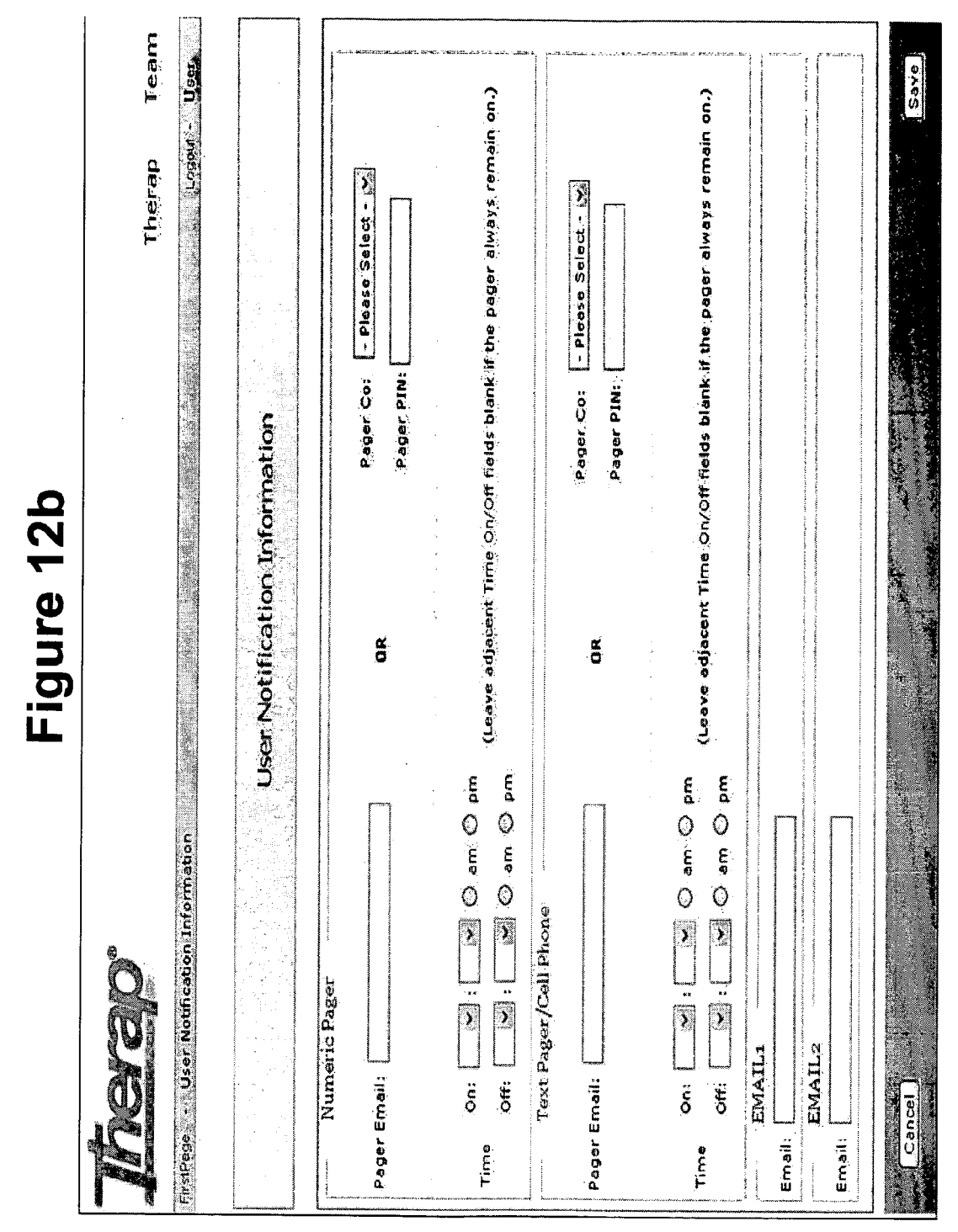

FIG. 12*b* is a screenshot of Notification Information. This displays the webpage that allows an authorized user to enter information required by the system in order to provide appropriate notifications to authorized users. Referring to FIG. 12*b* the invention allows the system to send notifications to authorized users according to the users' choice of notification media. The notification media that the system allows include Numeric Pager, Text Pager or Cell Phone, and Email.

FIG. 12*c* is a sample of the records in the notification profile which enable the system to securely alert authorized users of their services. Authorized users may configure their notification profiles according to their preferences. To configure notification profile, the users choose the appropriate application, from a list of applications they have access to, for which they want to configure. As shown in FIG. 12*c*, the users then may view the Configure Notification Profile page where they select the type of media and the degree of urgency of each media type depending on the user's needs.

FIG. 12*c*, for example shows the application or module 'General Event Reports' for which the notification profile may be configured. The section 'Notification Events' list the actions that are performed on general event reports. The 'Select Media' section in FIG. 12*c* lists the media types such as Numeric Pager, Text Pager/Cell Phone etc through which the system notifies the users. An authorized user then choose according to his/her preferences the notification events and the media type through which they want to receive the notifications. For example, an authorized user chooses the option 'Yes' for the Notification Event 'Submit'. Under Select Media the user then chooses the option 'Medium' beside the event 'Injury' under the media 'Text Pager/Cell Phone'. This means that the user is choosing to be notified through cell phone whenever a 'Submit' action is performed for the event 'Injury'. Choosing the notification level to be 'Medium' indicates that the user chooses to receive notifications of only those actions whose notification level is 'Medium' or 'High'. Thus the user is alerted of the authorized activities in the system appropriately. Hence, embodiments of the invention provide a system that enhances the efficiency of the user's work by immediately alerting the user about actions needing attention.

Figure 13:
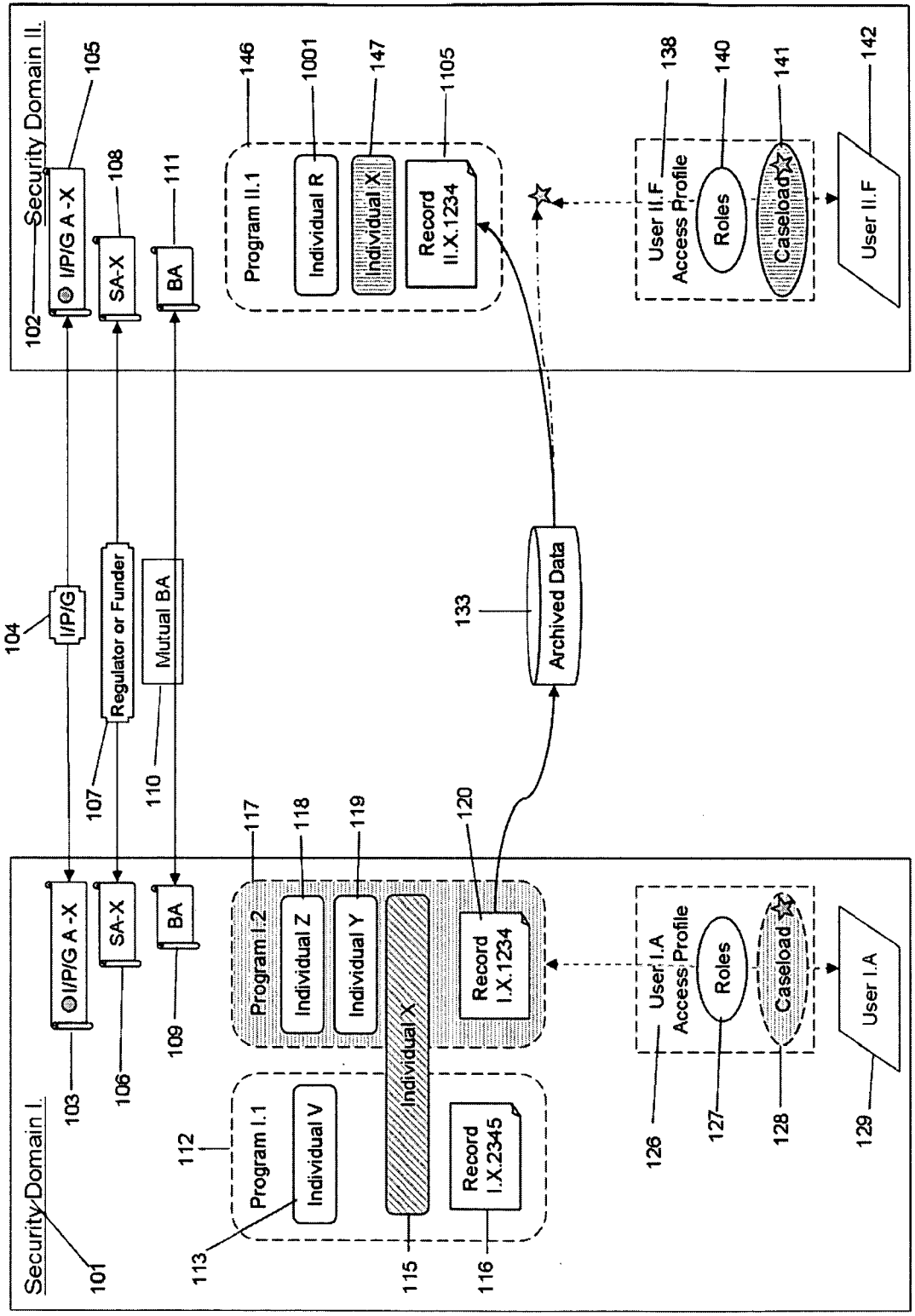
FIG. 13 illustrates embodiments of the system which provide Secure Access to Shared Archived Individual information.

FIG. 13 is an overview of embodiments of the invention which provide Secure Access to Archived Data in the system.

With the business agreement and proper authorizations in place, embodiments of this invention may allow users in the security domains to access Archived Data 133 of Individual X 115, 147. Embodiments of this invention provide systems to facilitate the archiving of data of Individuals when an organization chooses to send old data to archive to limit access. When an organization ceases to provide services to an Individual the records of the Individual may also be archived for future use and sharing.

Users with the proper roles may be allowed to access the archived information of Individuals. A user with an Update Archive Role may access appropriate records and update the information. With View Archive Role a user may view archived data 133 and copy data from the archive into an active record. Users with Send to Archive role may transfer specified data they have access to in the Archive.

As shown in the example in FIG. 13, User I.A 129 in Security Domain I 101 and User II.F 142 in Security Domain II 102 may be able to access archived information 133 of common Individuals—Individual X 115, 147. With the proper roles 127, User I.A 129 may send Record I.X.1234 120 to Archive 133, and User II.F 142 may in turn may access the Archived Data 113 and transfer it into an active record (Record II.X.1234 1105) in Security Domain II 102.

Figure 13A:
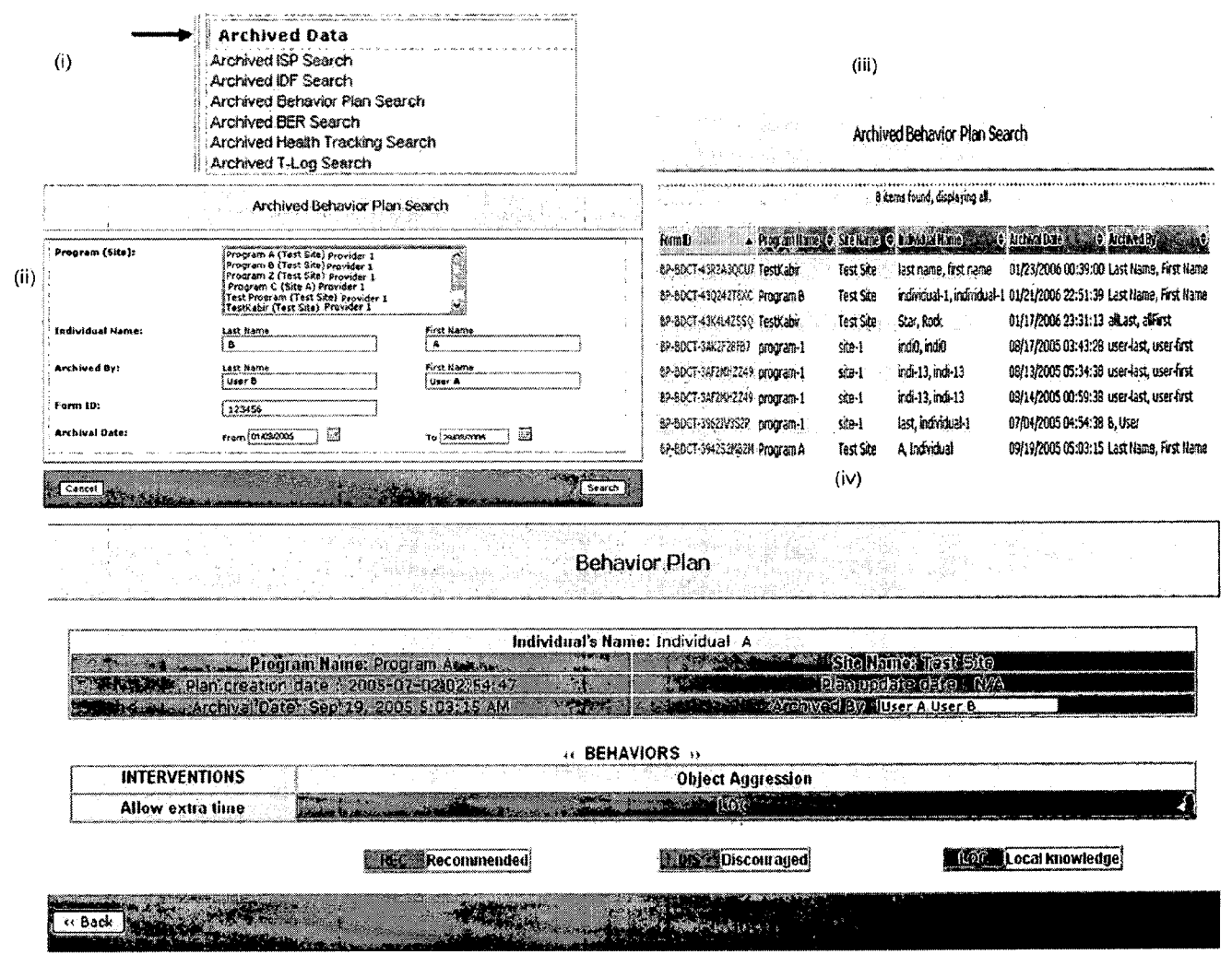

FIG. 13*a* is a sample of screenshots of the pages which enable authorized users to share and access Archived Data in a secure environment. The sample in FIG. 13*a* (I) shows the list of archived applications that may be available to users as per their roles and privileges. Clicking on a link allows an authorized user to enter a page (FIG. 13*a* (ii)) where they may search for archived data by Program, Individual Name, Form ID and Archive Date. Based on the criteria selected, a user with appropriate privileges can then view a list of records showing the archived information on the selected Individuals, as shown in FIG. 13*a* (iii). Referring to FIG. 13*a* (iv), users may then be able to view detailed information on the appropriate Individuals by clicking on one of these records. Embodiments of the invention allow users with appropriate roles to view, update, and send data to archives in a secure environment.

Figure 14:
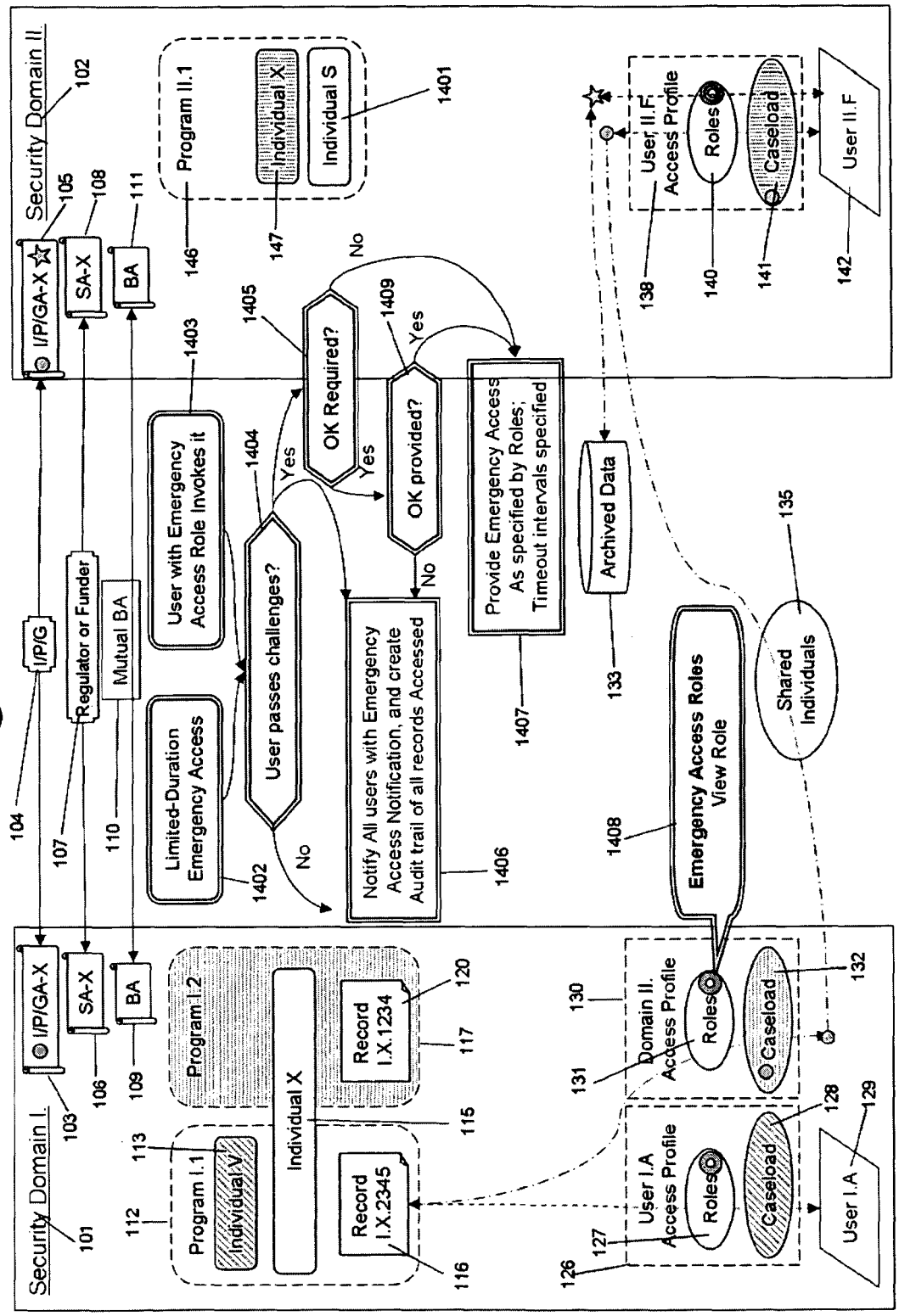
FIG. 14 illustrates embodiments of the system which provides Emergency Access so users can access defined Individual information in emergency situations.

FIG. 14 is an overview of embodiments of the Emergency Access features, which allow users to access certain Individual information in emergency situations.

In emergency situations staff members in an organization may not have access to certain information of Individuals which may be urgently needed. With the normal access privileges, users may not be able to access records beyond the privileges given by their Caseloads and Roles. The Emergency Access features may facilitate users in urgent situations by enabling them to gain access to selected information beyond their normal access privileges.

Embodiments of this invention provides a specific Emergency Data Form application to provide access to information which is typically needed in emergency situations, while releasing only a limited amount of private information. The Emergency Data Form is automatically updated when corresponding information is changed in any other application. In some cases it is desirable or required to have a printed version of the emergency information. Embodiments of the system may provide a role so that an authorized user is notified whenever the information on an Individual's Emergency Data Form changes so that they can print out a copy of the new version.

Referring to FIG. 14, Embodiments of this invention provide Emergency Access given to users in two different ways: Limited-Duration Emergency Access 1402, and Ongoing Emergency Access Role 1403 for a specified time interval. The only Role for the Emergency Data Form is the View Role 1408. Thus a user may be granted access to only this limited information about an Individual. This is appropriate for emergency services personnel, for people within the same organization who do not normally access information about this Individual, and for people in other organizations who may work with the Individual, but do not normally have access to information about the Individual in the Security Domain.

The Emergency Data Form View Role 1408 may be given to users as a normal part of working within a security domain. For example, selected users in organization may be given the Emergency Data Form View Role for a Caseload which comprises all the Individuals within the Security Domain, even though there normal Roles are limited to a subset of the Individuals and Programs.

Embodiments of the system also permit the Emergency Data Form View Role 1408 to be applied for sharing between Security Domains I 101 and II 102. In this case the Individuals to which it applies are limited to Shared Individuals 135, which in turn requires that the Security Domains have Individual/Parent/Guardian Authorizations (I/P/GA-X), Service Authorizations (SA-X), and a mutual Business Agreement (mutual BA). Thus there is a significant difference between an emergency access privileges provided as a user in the Security Domain versus one that is implemented through information sharing among Security Domains.

A Limited Duration Emergency Access 1402 account may be created by an appropriately authorized Data Administrator. When an emergency occurs, a user may gain access to this account in various ways. For example, someone desiring access, such as emergency services personnel, can contact an appropriate person in the corresponding security domain to obtain the information required to access the emergency account. Alternatively, the emergency services organization may have the access information on file and only use it in cases of an emergency. The Data Administrator may identify the access accounts, for example, using the name of the emergency services or organization, or the name of specific potential users, such as a Fire Chief or the Commissioner of Division of Developmental Disability Services (DDDS).

When an account is first used, embodiments of the system may permit the Security Domain to display specific information to the user, and may require questions to be answered by the user before the account can be used. For example, the user may have to signify that they have read and understood the displayed text; also the user may have to enter data such as the user's name, organization affiliation, and position. These are the challenges a user faces referred to in FIG. 14 as 1404 and 1405. Embodiments of the system allow a Data Administrator to specify that an account may be deactivated after its first use, a given number of uses, or a period of time.

Referring to FIG. 14, embodiments of this invention may therefore allow User I.A 129 to access Record I.X.2345 116 of Individual X 115 in Program I.1 112. Emergency Access may also apply to Shared 135 or Archived Data 133 for Individuals 135 in the users' Caseloads (128, 132, 141, and 144). Therefore, embodiments of this invention may also allow User II.F 142 to access Record I.X.1234 120 in Program I.2 117. These privileges are given to users with the proper Emergency Access roles 1408.

A Data Administrator can choose to be notified as stated in 1406, when an account is first used, or when an Emergency Data Form View Role is used. A Data Administrator may track the actions of any account as they occur, for example as shown in FIG. 11*a*. The Data Administrator may deactivate the account at any time, including while the account is in use. Thus a Data Administrator has considerable flexibility in creating and managing a Limited Duration Emergency Access 1402 account, and use of the Emergency Data Form View Role 1408.

Figure 14A:
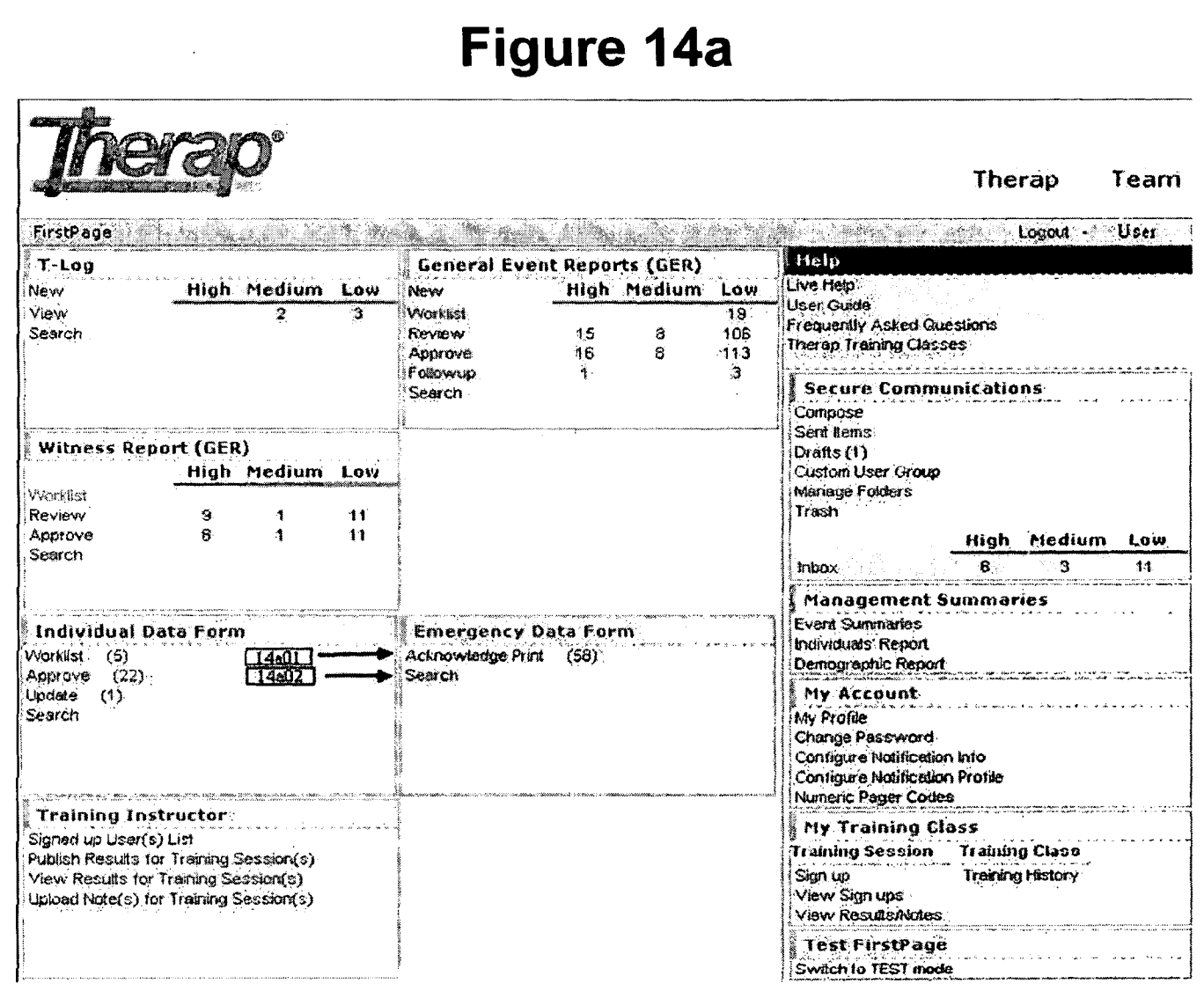

FIG. 14*a* is a sample of the FirstPage showing the Emergency Data Form Role. The Emergency Data Form has been designed to display the Individual information that is commonly requested to carry out activities in emergency cases. As shown in FIG. 14*a*, authorized users have only Emergency Form View Role that allows them to access, view, and if necessary print the information about the Individual's Identification, Contact, Medical, and Insurance within a secure environment. With the aid of such information, embodiments of the invention facilitate the system to recognize authorized users in emergency situations, and may control their access to other information.

FIG. 15 is a sample of Additional Shared Security Features that enhances privacy in sharing.

Each Security Domain involved in sharing common Individual information has its own Password Policy, specifying variables to define the policies. As shown in FIG. 15, authorized users in Security Domain—Provider A may define their organization's own Password Policy specifying the limitations of the variables. Thus, embodiments of the invention allow each provider to set their own password policy to maintain secure information sharing.

Embodiments of the system may include requirements of the password policy configuration, as shown in FIG. 15: the minimum length of the password, the minimum number of uppercase letters, the minimum number of digits, the minimum number of other characters, the maximum number of incorrect password attempts before the account is locked, the timeframe in which the password attempts are measured, the expiration date of the password, and the starting day of warning a user before expiration of the password.

Figure 15A:
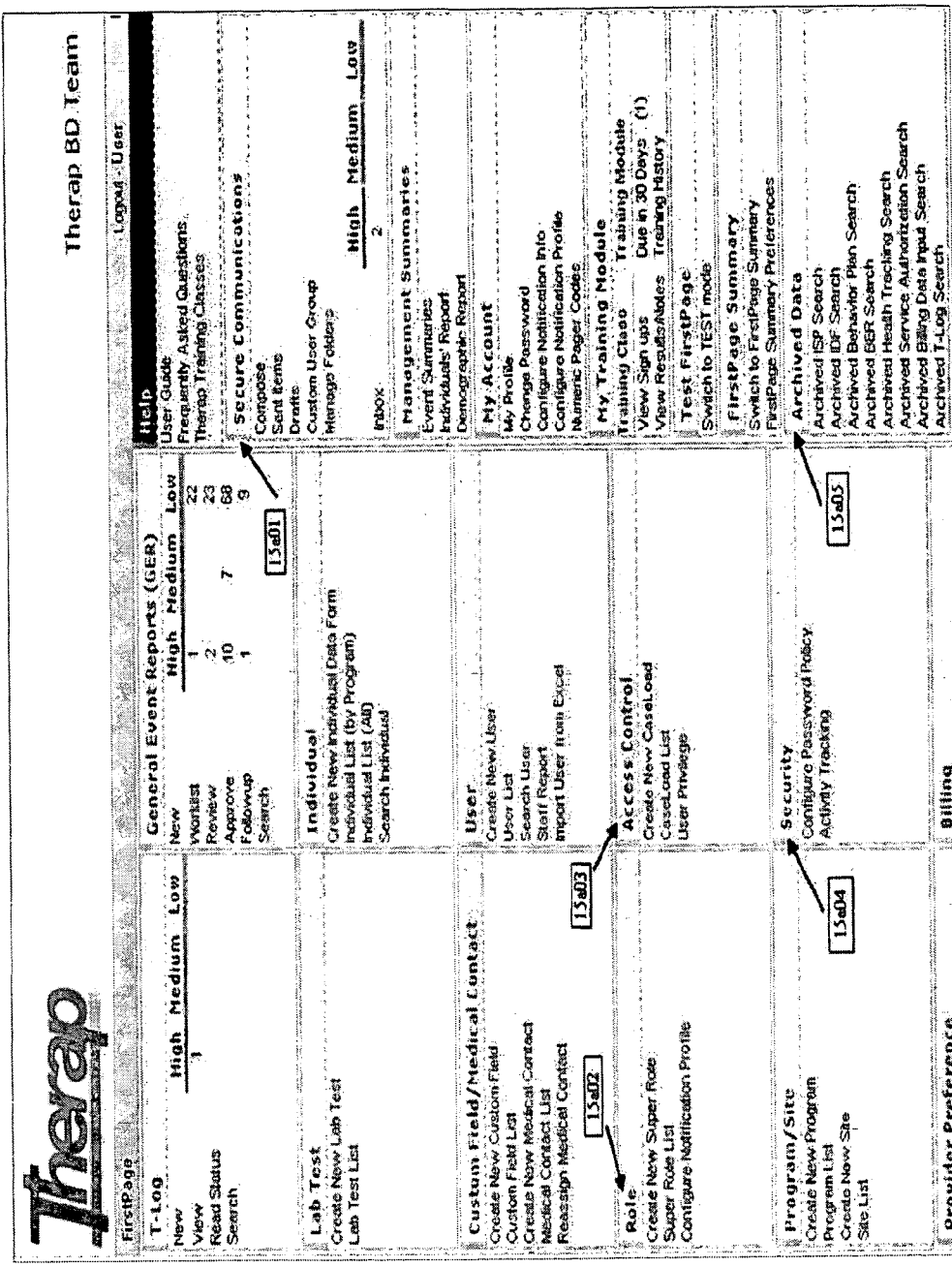
FIG. 15a is a sample of other Additional Shared Security Features that facilitate information sharing by providing privacy and security.

FIG. 15*a* is a sample of other Additional Shared Security Features that facilitates in information sharing by providing privacy and security by enabling a Data Administrator to manage all of these security access features.

As shown in the figure, embodiments of the invention provide each Security Domain the privilege to define (1) Super Roles—defining the extent of roles, (2) Caseloads—defining who may have what privileges on which program and/or individual, (3) Sharing—sharing individual information among organizations, (4) Archiving—storing individual information that may be shared by organizations having appropriate agreements, and (5) Emergency characteristics that may be used to categorize the system's actions.

Referring to FIG. 15*a*, the arrow 15*a*01 refers to the module 'Secure Communications' which is a secure E-mail system provided to authorized users. The system allows the users through Secure Communications to securely exchange Personal Health Information (PHI) and other confidential information in compliance with HIPAA. The arrow 15*a*02 refers to roles and super roles that define the extent of user authorization. The arrow 15*a*03 refers to the module 'Access Control' that is designed to restrict the user privilege. The arrow 15*a*04 refers to the module 'Security' that allows authorized Security Domains or organizations to configure their password policy. Through this module, the system also tracks the time and date each activity is taking place within the system. The arrow 15a05 refers to the module 'Archived Data' that stores all the old data that had been modified or updated by authorized users. The modified information are not only stored but also can be retrieved and viewed in future for further use.

Figure 16:
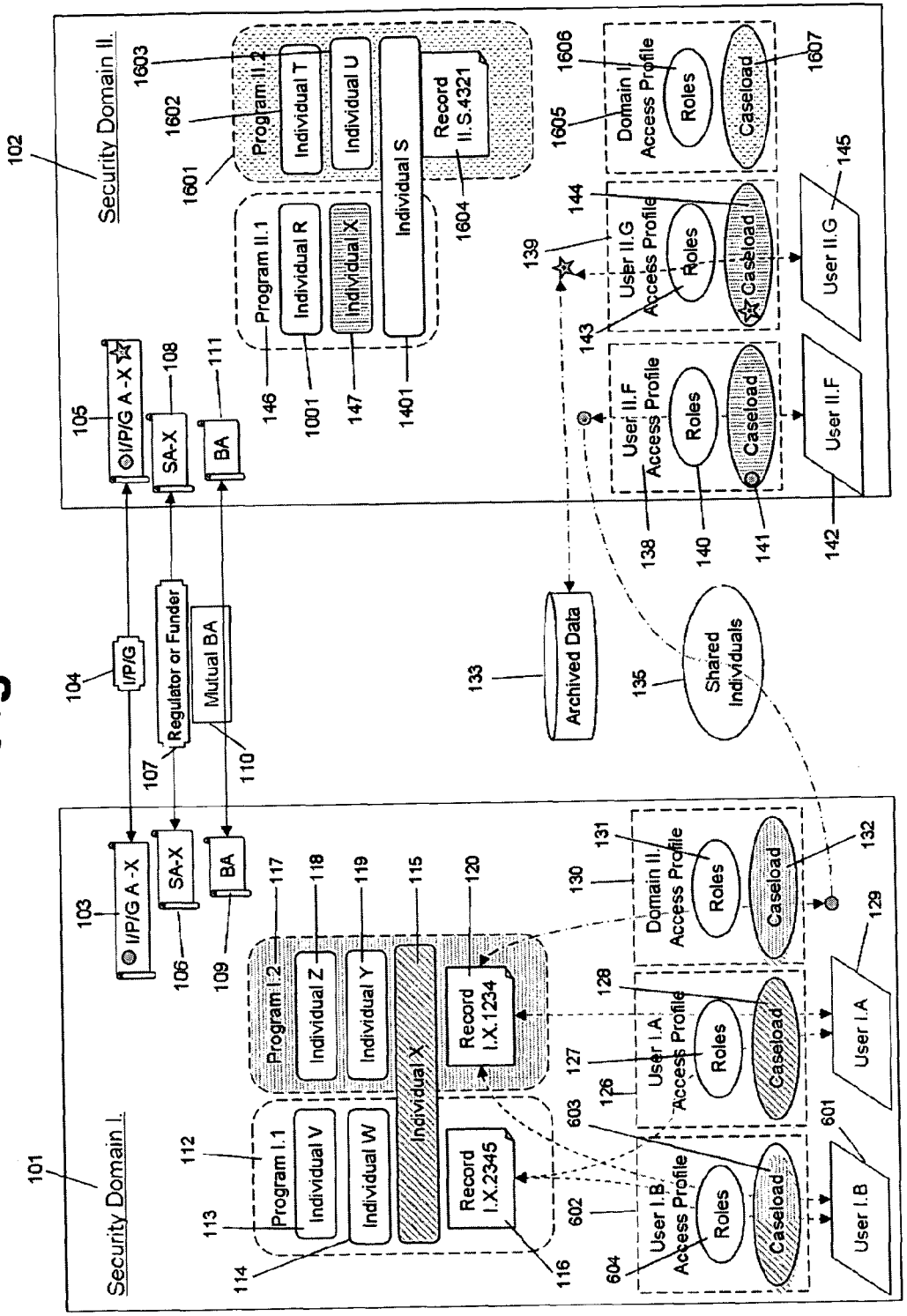
FIG. 16 illustrates embodiments of the Security Monitoring and Auditing for Shared Access to track the access of Individual information for privacy and security as requested by HIPAA regulations and guidelines.

FIG. 16 is an overview of embodiments of the Security Monitoring and Auditing system for Shared Access which enhance privacy and security of Individual information as requested by HIPAA regulations and guidelines.

Security Domain I 101 and Security Domain II 102 represent two organizations that have the Individual, Parent, and/or Guardian authorizations 103 and 105 to support and share information of common Individuals among them. The organizations have been granted service authorizations 106 and 108 by the Regulator or Funder 107. The organizations also have a new mutual business agreement 110 in effect.

Referring to FIG. 16 Individual S 1401 is enrolled in both the programs Program II.1 146 and Program II.2 1601 in Security Domain II 102. In addition, Program II.1 146 has Individual R 1001 and Program II.2 1601 has Individual T 1602 and Individual U 1603 enrolled, in Security Domain II 102. Each organization under the agreement has a Sharing Access Profile 130 and 1605 of the other.

Security Domain II 102 has the Access profile 139 of User II.G 145 allowing the user to have access privileges 144 on the archived data 133 of Individual X 115. Security Domain II 102 also has Access Profile 1605 of Domain I 101 that allows users to access information on Program II.2 1601 in Security Domain II 102 and thus share information on common Individuals among the organizations Security Domain I 101 and Security Domain II 102.

In order to wholly comply with, inter alia, HIPAA security regulations and guidelines on health information of Individuals, embodiments of the invention keep track of every access to the system. Systems are provided to track every detail of actions performed on any data. Any access to the system or any action performed is logged, including Archived 133 and Shared 135 access, noting User ID, time, date, data ID, and activity. All the activities of staffs may be carefully monitored to ensure that information has been shared and accessed as permitted by their privileges. Security Domain staff with proper authorizations may be notified of all activities as specified in their profiles.

In addition, embodiments of the invention provide systems to continuously monitor all activities for suspicious patterns. Any undesired actions by authorized or unauthorized people may notify the appropriate security domain staff and Therap Services, who may take direct action that includes disabling user accounts, freezing selected data, or terminating the privileges of a Security Domain.

Figure 16A:
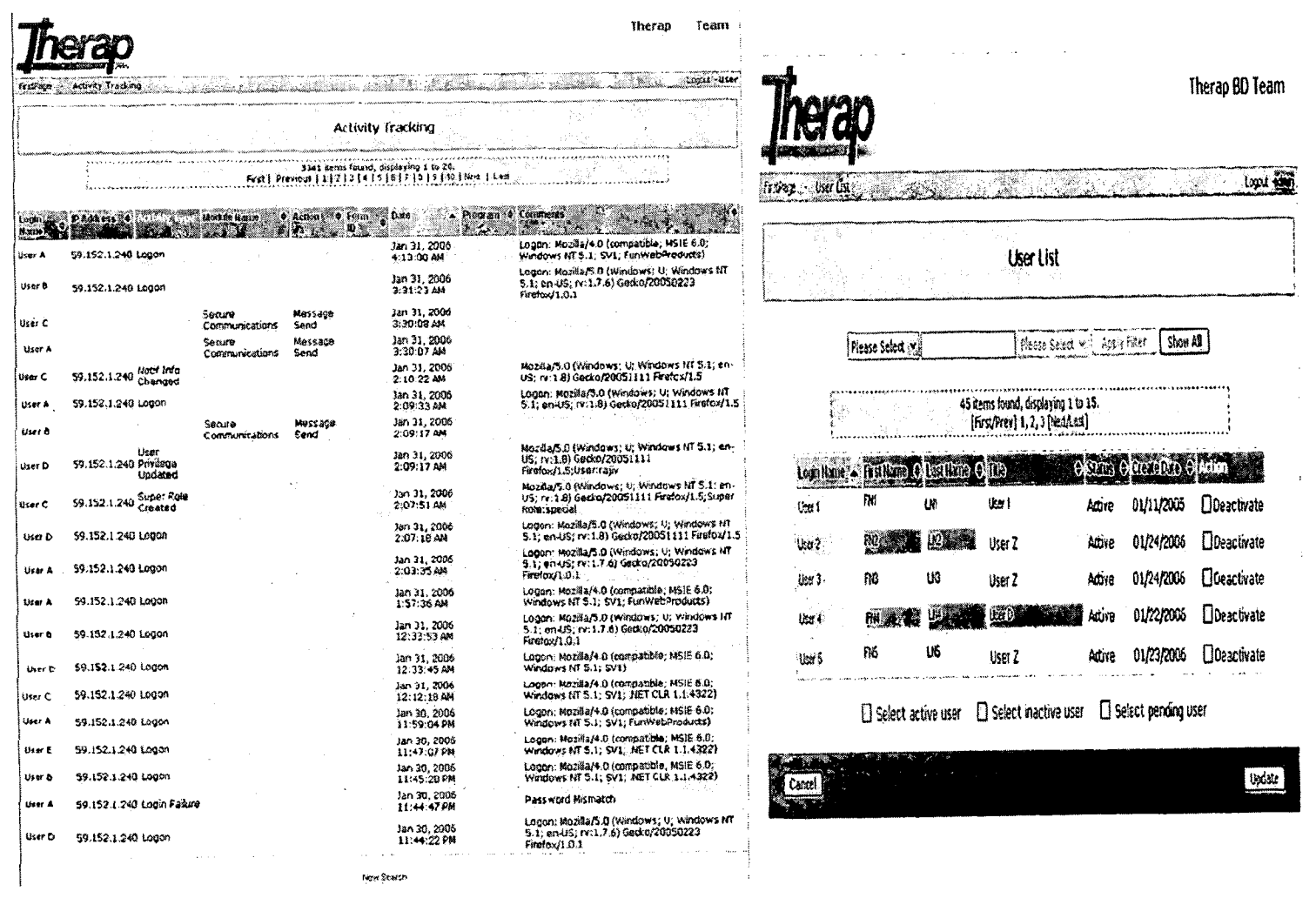

FIG. 16a is a sample of the pages which enable systems for Security Monitoring and Auditing for Shared Access. Organizations with appropriate agreements in effect share individual information that is subject to change by authorized users. To provide data consistency while sharing individual information, embodiments of the invention provide systems that record detailed information about the activities of the authorized users to ensure security and privacy. Embodiments of the invention allow a system Activity Tracking that stores information about the authorized users to track down the user's activities on the system. The screen on the left of FIG. 16a is the Activity Tracking page that shows records of the users' login name, Internet Protocol (IP) address, activity type, module name, action, date and time, and programs. These data may assist in tracking down the causes of changes in information when requested.

In order to comply with, inter alia, HIPAA regulations, the system also may monitor all activities to detect any suspicious patterns as mentioned in I1603 in FIG. 16. The system administrator is authorized to take direct actions against acts that violate the health related laws and regulations. The right side of FIG. 16a represents a page User List where the user Admin has the privilege to disable any user accounts, if found to be performing activities accounting against, for example, HIPAA regulations, by clicking on Deactivate on the right side of each user's record. Thus, embodiments of the invention ensure privacy and security while sharing individual information within and across organizations having Mutual Business Agreement and appropriate authorizations in effect.

Figure 17:
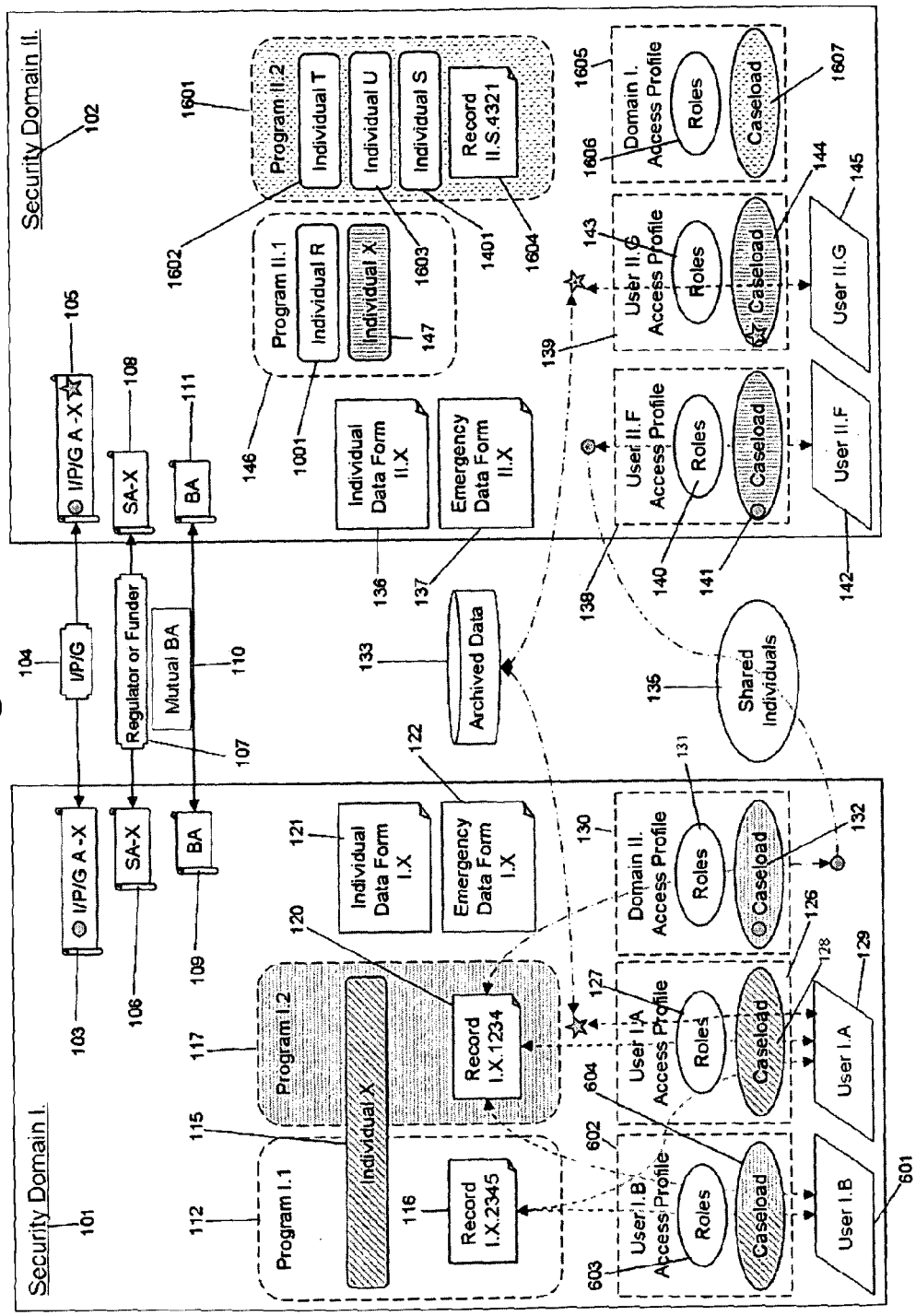
FIG. 17 illustrates an overview of Shared System having Individual, Guardian or Parent as Primary Security Domain Manager.

FIG. 17 illustrates the Secure Shared Information Access where the Individual, Parent or Guardian acts as the Primary Security Domain manager.

Embodiments of the present invention provide secure sharing of private health information across organizations in accordance with HIPAA and other security regulations.

As shown in FIG. 17, Security Domain I 101 represents the Individual, Parent or Guardian 104 acting as the Primary Security Domain manager having service authorizations 106 and 108 from Regulators or Funders 107 that define the services which can be supplied for the Individual. Security Domain I 101, being an Individual, Parent and/or Guardian 104 themselves, does not require Individual or Guardian authorization, thus making the secure Individual information sharing more flexible. Security Domain II 102 represents an organization that has a valid Individual, Parent or Guardian Authorization 108 to store or access private information about the Individual, and also to share information with another organization or Parent/Guardian 104 acting as a service provider. In order to share common Individual information among the service providers, they must enter into a Business Agreement 110, which complies with privacy, and security regulations in accordance with HIPAA and other state laws.

Referring to FIG. 17 Individual X 115 represents an Individual who is served by both security domains, Security Domain I 101 and Security Domain II 102. Both the security domains have the required detailed information of Individual X 115 in Individual Data Form I.X 121 and Emergency Data Form I.X 122 in Security Domain I 101 and Individual Data Form II.X 136 and Emergency Data Form II.X 137 in Security Domain II 102. In Security Domain I 101, Individual X 115 is enrolled in two service Programs, termed as Program I.1 112 and I.2 117. The same Individual in Security Domain II 102 is enrolled in Program II.1 146. Each security domain under the agreement has a Sharing Access Profile 130 and 1605 of the other. This invention includes innovative mechanisms to identify common Individuals and their corresponding health information that is to be shared.

Embodiments of this invention include mechanisms allowing authorized users in one organization to access Individual information under different security domains within that organization. Authorized users in Security Domains I 101 and II 102 are assigned access privileges or roles that control users' access to specific Individual information. Access privileges define the extent to which a user can access and/or perform actions on Individual information. This invention includes an innovative mechanism, Caseloads (128, 132, 141, 144, 604, 1607), which allow the Security Domains I 101 and II 102 to specify access capabilities of the user on a combination of one or more programs, Individuals, program-Individual pair, or other predefined caseloads. This capability ensures flexibility and facilitates the privacy and security mechanisms by allowing users to have privileges for only one Individual or several Individuals not aligned with the conventional programs or for users who have privileges only for one Individual.

As shown in FIG. 17, the Individual, Parent and/or Guardian 104, being one of the Security Domain managers, will gain complete access and control on the Individual information securely within the homely environment. This revolutionary act gives them the privilege to be informed of all the actions performed on the Individual information in a secure environment. This invention facilitates Security Domains I 101 and II 102 by ensuring security and privacy in sharing and manipulating Individual information in compliance with HIPAA regulations and other state laws.

Referring to FIG. 17, User I.A 129 and I.B 601 are authorized users in Security Domain I 101, and User II.F 142 and User II.G 145 are authorized users in Security Domain II 102. Each will have similar or different access profiles under the security domains they are in. User I.A 129 in Security Domain I 101 has access privileges on Individual X 115. This means that the invention will allow User I.A 129 to access records of Individual X 115 irrespective of the programs s/he is enrolled in. That is User I.A 129 can access Record I.X.2345 116 in Program I.1 112 and Record I.X.1234 120 in Program I.2 117 of Individual X 115. User I.B 601 has access privileges on Individual X 115 and Program I.2 117. This invention will allow User I.B 601 to access records of all Individuals (including Individual X 115) in Program I.2 117 and other records of Individual X 115 irrespective of the program s/he is enrolled in. This will allow User I.B 601 to access Record I.X.2345 116 in Program I.1 112 and Record I.X.1234 120 in Program I.2 117 of Individual X 115. However, Security Domain I 101, being the Individual, Parent and/or Guardian 104, comprises of only one individual— Individual X 115.

User II.F 142 in Security Domain II 102 has privileges to access information of Individual X 115. The Access Profile 130 of Domain II 102 in Security Domain I 101 defines privileges for users in Security Domain II 102 to access information of common Individuals in Program I.2 117 of Security Domain I 101. The invention has mechanisms to determine the common Individuals across the organizations. Through this mechanism the Access Profile 130 of Domain II 102 in Security Domain I 101 will allow User II.F 142 in Security Domain II 102 to have access privileges 141 on Individual X 115 in Program I.2 117 in Security Domain I 101. Thus User II.F 142 in Security Domain II 102 will have access to Record I.X.1234 120 in Program I.2 117 in Security Domain I 101 of Individual X 115.

Access profile 139 of User II.G 145 in Security Domain II 102 will allow the user to have access privileges on the archived data 133 of Individual X 115. Archived data 133 of Individuals include records that are updated or changed, or the old data that an organization chooses to send to archive. When an organization ceases to provide services to an Individual the records of the Individual can also be archived for future use and sharing. Authorized users, given appropriate archive roles, can access and retrieve information from the archived data of Individuals.

We claim:

1. A method of authorizing access by users to at least one individual's information stored by an organization as associated with at least one program and at least one security domain, comprising:
    defining a first caseload as including access privilege information associated with a first security domain for at least one of a first individual and a first medical services program,
    defining a second caseload as including access privilege information associated with a second security domain of at least one of a second individual and a second medical services program,
    defining a third caseload as including access privilege information associated with said first security domain and said second security domain of at least said first program and said second program,
    requesting authorization from the organization for the user to access one or more of said caseloads,
    logging by one or more physical nodes, in an activity log associated with at least the first medical services program or the second medical services program, said request for authorization for the user to access one or more of said caseloads,
    determining by the one or more physical nodes whether the user is authorized to access said privilege information associated with said one or more of said caseloads, wherein the determination is based on at least the one or more caseloads and the personal health information of the one or more individuals in the organization, and
    granting access to the user to one or more of said caseloads.

2. A method as in claim 1 wherein the request for access is a request to view the information.

3. A method as in claim 1 wherein the request for access is a request to modify the information.

4. A method as in claim 1 wherein the request for access is a request to save the information.

5. A method as in claim 1 wherein the request for access is a request to submit the information.

6. A method of authorizing access by users to at least one database of information stored by an organization as associated with at least one program and at least one security domain, comprising:
    defining a first caseload as including access privilege information associated with a first security domain of at least one first database of information of a first program,
    defining a second caseload as including access privilege information associated with a second security domain of at least one second database of information of a second program,
    defining a third caseload as including access privilege information associated with said first security domain and said second security domain of at least said first database of information of said first program and said second database of information of said second program,
    requesting authorization from the organization for the user to access one or more of said caseloads,
    logging by one or more physical nodes, in an activity log associated with at least the first database of information or the second database of information, said request for authorization for the user to access one or more of said caseloads,
    determining by the one or more physical nodes whether the user is authorized to access one or more of said databases of information associated with said one or more of said caseloads, wherein the determination is based on at least the one or more caseloads and the personal health information of the one or more individuals in the organization, and
    granting access to the user to one or more of said caseloads.

7. A method as in claim 6 wherein the request for access is a request to view the information.

8. A method as in claim 6 wherein the request for access is a request to modify the information.

9. A method as in claim 6 wherein the request for access is a request to save the information.

10. A method as in claim 6 wherein the request for access is a request to submit the information.

* * * * *